United States Patent [19]

Naka et al.

[11] Patent Number: 5,162,326
[45] Date of Patent: Nov. 10, 1992

[54] PYRIMIDINEDIONE DERIVATIVES, THEIR PRODUCTION AND USE

[75] Inventors: Takehiko Naka, Hyogo; Kohei Nishikawa, Kyoto, both of Japan

[73] Assignee: Takeda Chemical Industries, Ltd., Osaka, Japan

[21] Appl. No.: 654,490

[22] Filed: Feb. 13, 1991

[30] Foreign Application Priority Data

Feb. 15, 1990 [JP] Japan .................. 2-034919

[51] Int. Cl.$^5$ .................. A61K 31/505; C07D 239/02
[52] U.S. Cl. ...................... 514/269; 514/86; 514/235.8; 514/253; 544/123; 544/243; 544/295; 544/300; 544/309; 544/310; 544/311; 544/312; 544/313; 544/314
[58] Field of Search ............... 544/300, 310, 243, 123, 544/295, 309, 311, 312, 313, 314; 514/269, 86, 235.8, 253

[56] References Cited

U.S. PATENT DOCUMENTS 4,880,804 11/1989 Carini et al. .................. 514/253

FOREIGN PATENT DOCUMENTS 0028833 5/1981 European Pat. Off. .
0028834 5/1981 European Pat. Off. .
0245637 11/1987 European Pat. Off. .
0253310 1/1988 European Pat. Off. .
0291969 11/1988 European Pat. Off. .
0323841 7/1989 European Pat. Off. .

Primary Examiner—Cecilia Tsang
Attorney, Agent, or Firm—Wegner, Cantor, Mueller & Player

[57] ABSTRACT

Novel pyrimidinedione derivatives of the formula (I):

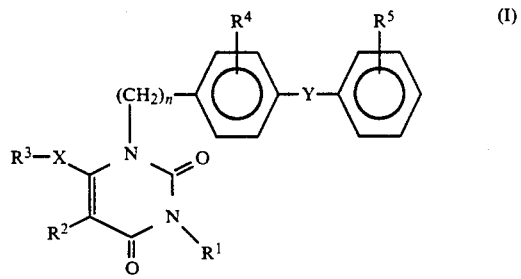

wherein $R^1$ is hydrogen or a hydrocarbon residue which may be substituted; $R^2$ is hydrogen, halogen, nitro, optionally substituted amino, formyl or a hydrocarbon residue which may be substituted; $R^3$ is a hydrocarbon residue which may be substituted; $R^4$ is hydrogen, halogen or nitro; $R^5$ is a residue capable of forming an anion or a residue convertible into an anion; X is a direct bond or a spacer having one atomic length and containing an oxygen, nitrogen or sulfur atom; Y is a direct bond or a spacer having atomic length of two or less between the phenylene group and the phenyl group; n is an integer of 1 or 2; and the pharmaceutically acceptable salts thereof have potent angiotensin II antagonistic activity and hypotensive activity, thus being useful as therapeutic agents for treating circulatory system diseases such as hypertensive diseases, heart diseases, strokes, etc.

23 Claims, No Drawings

PYRIMIDINEDIONE DERIVATIVES, THEIR PRODUCTION AND USE

FIELD OF THE INVENTION

The present invention relates to novel pyrimidinedione derivatives having potent pharmacological activity and intermediates for the preparation thereof. More particularly, the present invention relates to compounds having potent angiotensin II antagonistic activity and hypotensive activity, which are useful as therapeutic agents for treating circulatory system diseases such as hypertensive diseases, heart diseases, strokes, etc.

BACKGROUND OF THE INVENTION

The renin-angiotensin system is involved in the homeostatic function to control systemic blood pressure, the volume of body fluid, balance among the electrolytes, etc., associated with the aldosterone system. Development of angiotensin II converting enzyme inhibitors (ACE inhibitor) (this converting enzyme produces angiotensin II which possesses strong vasoconstrictive activity) has clarified the relation between the renin-angiotensin system and hypertension. Since angiotensin II elevates blood pressure via the angiotensin II receptors on cell membranes, angiotensin II antagonists as well as the ACE inhibitor would be useful in treating hypertension.

It has been reported that various angiotensin II analogues such as saralasin, [$Sar^1$, $Ile^8$]A II, and the like, possess potent angiotensin II antagonistic activity.

It has, however, been reported that, when peptide antagonists are administered parenterally, their actions are not prolonged and, when administered orally, they are ineffective (M. A. Ondetti and D. W. Cushman, Annual Reports in Medicinal Chemistry, 13, 82–91 (1978)).

Non-peptide angiotensin II antagonists are disclosed in Japanese Patent Laid Open No. 71073/1981; No. 71074/1981; No. 92270/1982; No. 157768/1983; No. 23868/1988; and No. 117876/1989, etc.

Imidazole derivatives having angiotensin II antagonist activity are disclosed in A. T. Chiu et al., Eur. J. Pharm., 157, 13 (1981), P. C. Wong et al., J. Pharmcol. Exp. Ther., 247, 1 (1988), P. C. Wong et al., Hypertension, 13, 489 (1989), etc.

It has not yet been known that pyrimidinedione derivatives possess potent angiotensin II antagonist activity.

SUMMARY OF THE INVENTION

The present inventors made extensive investigations to prepare useful compounds which have angiotensin II antagonistic activity. As a result of these researches, the present inventors have succeeded in synthesizing pyrimidinedione derivatives possessing excellently potent angiotensin II antagonistic activity and developed their work to accomplish the present invention.

The present invention provides pyrimidinedione derivatives having the formula I:

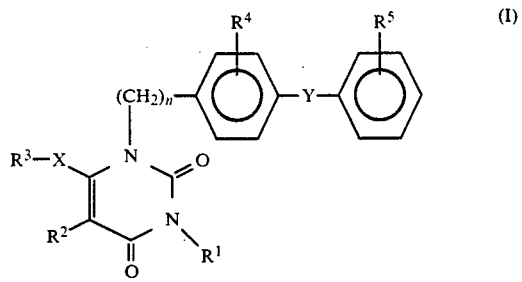

wherein
$R^1$ is hydrogen or a hydrocarbon residue which may be substituted;
$R^2$ is hydrogen, halogen, nitro, optionally substituted amino, formyl or a hydrocarbon residue which may be substituted;
$R^3$ is a hydrocarbon residue which may be substituted;
$R^4$ is hydrogen, halogen or nitro; $R^5$ is a residue capable of forming an anion or a residue convertible into an anion;
X is a direct bond or a spacer having one atomic length and containing an oxygen, nitrogen or sulfur atom;
Y is a direct bond or a spacer having atomic length of two or less between the phenylene group and the phenyl group; and
n is an integer of 1 or 2;
and the pharmaceutically acceptable salts thereof.

These compounds are potent angiotensin II antagonists which are of value in the treatment of circulatory system diseases such as hypertensive diseases, heart diseases, strokes, etc.

Another aspect of the present invention relates to pharmaceutical compositions comprising an effective amount of the pyrimidinedione derivative having the formula I and a pharmaceutically acceptable carrier useful in treating circulatory system diseases such as hypertensive diseases, heart diseases, strokes, etc., and processes for preparing such compounds and compositions.

Still another aspect of the present invention relates to a method for treating said circulatory system diseases of hosts, which comprises administering an effective amount of the pyrimidinedione derivative having the formula I or the pharmaceutical composition thereof to said host.

DETAILED DESCRIPTION OF THE INVENTION

The present invention provides pyrimidinedione derivatives having the formula I and the pharmaceutically acceptable salts thereof, which possess potent angiotensin II antagonistic activity and are of value in the treatment of circulatory system diseases such as hypertensive diseases, heart diseases, strokes, etc., pharmaceutical compositions comprising an effective amount of the pyrimidinedione derivative having the formula I and a pharmaceutically acceptable carrier useful in treating said circulatory system diseases and processes for preparing such compounds and compositions.

The present invention further provides a method for treating said circulatory system diseases of hosts, which comprises administering an effective amount of the pyrimidinedione derivative having the formula I or the pharmaceutical composition thereof to said host.

With regard to the foregoing formula (I), hydrocarbon residues for $R^1$ include acyclic hydrocarbon residues, aryl and aralkyl groups.

Such hydrocarbon residues for $R^1$ include lower alkyl of 1 to about 8 carbon atoms and lower alkenyl of 2 to about 8 carbon atoms, which may be straight or branched.

Examples of hydrocarbon residues for $R^1$ include methyl, ethyl, vinyl, propyl, propenyl, isopropyl, butyl, isobutyl, sec-butyl, t-butyl, pentyl, i-pentyl, hexyl, heptyl, octyl, octenyl, and the like.

Said hydrocarbon residues for $R^1$ may be optionally substituted with 1 to 3 substituents selected from halogen (e.g. F, Cl, Br and the like), nitro, cyano, optionally substituted amino [e.g. amino, N-lower ($C_{1-4}$) alkyl amino (e.g. methylamino, and the like), N,N-dilower ($C_{1-4}$) alkyl amino (e.g. dimethylamino, and the like), N-arylamino (e.g. phenylamino, and the like), N-aralkylamino (e.g. benzylamino, naphthylmethylamino, and the like), N-heteroarylamino (e.g. pyridylamino, and the like), N-heteroaralkylamino (e.g. pyridylmethylamino, and the like), alicyclic amino (e.g. morpholino, piperidino, piperazino, piperidylmethyl, N-phenylpiperazino, N-(p-fluorophenyl)-piperazino, and the like), etc., wherein said alkyl, aryl and heteroaryl groups may be optionally substituted with lower ($C_{1-4}$) alkyl (e.g. methyl, ethyl, propyl, isopropyl, butyl, isobutyl, sec-butyl, and the like), hydroxyl, optionally substituted amino (e.g. amino, N-lower ($C_{1-4}$) alkyl amino (e.g. methylamino, ethylamino, and the like), N,N-dilower ($C_{1-4}$) alkyl amino (e.g. dimethylamino, and the like), alicyclic amino (e.g. morpholino, piperidino, piperazino, N-phenylpiperazino, and the like), etc), halogen, nitro, lower ($C_{1-4}$) alkoxycarbonyl (e.g. methoxycarbonyl, ethoxycarbonyl, and the like), lower ($C_{1-4}$) alkoxy (e.g. methoxyl, ethoxyl, and the like), etc.], a group having the formula: —COD, and the like, wherein D is alkoxy, hydroxyl, halogen, optionally substituted amino as defined above [e.g. amino, N-lower ($C_{1-4}$) alkyl amino (e.g. methylamino), N,N-dilower ($C_{1-4}$) alkyl amino (e.g. dimethylamino), N-arylamino (e.g. phenylamino), N-aralkylamino (e.g. benzylamino and naphthylmethylamino), N-heteroarylamino (e.g. pyridylamino), N-heteroaralkylamino (e.g. pyridylmethylamino), and alicyclic amino (e.g. morpholino, piperidino, piperazino, piperidylmethyl, N-phenylpiperazino, N-(p-fluorophenyl)piperazino, etc.), wherein said alkyl, aryl and heteroaryl groups may be optionally substituted with lower ($C_{1-4}$) alkyl (e.g. methyl, ethyl, propyl, isopropyl, butyl, isobutyl, sec-butyl, and the like), hydroxyl, optionally substituted amino as defined above (e.g. amino, N-lower ($C_{1-4}$) alkyl amino (e.g. methylamino, ethylamino, and the like), N,N-dilower ($C_{1-4}$) alkyl amino (e.g. dimethylamino, and the like), alicyclic amino (e.g. morpholino, piperidino, piperazino, and N-phenylpiperazino), and the like), halogen, nitro, lower ($C_{1-4}$) alkoxycarbonyl (e.g. methoxycarbonyl, ethoxycarbonyl, and the like), lower ($C_{1-4}$) alkoxy (e.g. methoxyl, and ethoxyl), etc], or the like.

Examples of aryl groups for $R^1$ include phenyl, naphthyl and the like. Said aryl groups may be optionally substituted with 1 to 3 substituents selected from halogen (e.g. F, Cl, Br and the like), nitro, lower ($C_{1-4}$) alkyl (e.g. methyl, ethyl, and the like), and the like at an optional position on the ring.

Examples of aralkyl groups for $R^1$ include phenyl-lower ($C_{1-4}$) alkyl such as benzyl, phenethyl, and the like. Said aralkyl groups may be optionally substituted with 1 to 3 substituents selected from halogen (e.g. F, Cl, Br and the like), nitro, lower ($C_{1-4}$) alkyl (e.g. methyl, ethyl, and the like), and the like at an optional position on the ring.

The halogen for $R^2$ includes fluorine, chlorine, bromine, and iodine.

The optionally substituted amino groups for $R^2$ include a group having the formula: —$NHR^6$, a group having the formula:

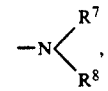

and the like, wherein $R^6$ is an acyl group of 1 to about 8 carbon atoms derived from fatty acid (e.g. formyl, acetyl, propionyl, butyryl, and the like), and $R^7$ and $R^8$ each is independently hydrogen, lower alkyl of 1 to about 8 carbon atoms (e.g. methyl, ethyl, propyl, butyl, and the like) or an acyl group of 1 to about 8 carbon atoms derived from fatty acid (e.g. formyl, acetyl, propionyl, butyryl, and the like).

The hydrocarbon residues for $R^2$ include acyclic hydrocarbon residues, aryl and aralkyl groups.

Examples of such acyclic hydrocarbon residues for $R^2$ include alkyl of 1 to about 8 carbon atoms and alkenyl of 2 to about 8 carbon atoms.

The substituted acyclic hydrocarbon residues for $R^2$ include acyclic hydrocarbon residues substituted with nitrile, carbamoyl, aryl (e.g. phenyl, and the like), hydroxyl, carboxyl, ester (e.g. $C_{2-5}$ alkanoyloxy, $C_{1-4}$ alkoxycarbonyl, and the like), optionally substituted amino (e.g. amino, lower ($C_{1-4}$) alkylamino, di-lower ($C_{1-4}$) alkylamino, $C_{2-5}$ alkanoylamino, and the like), or the like.

Examples of said substituted hydrocarbon residues for $R^2$ include groups having the formula:

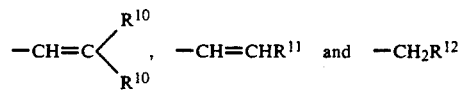

wherein $R^{10}$ is nitrile, carbamoyl, or alkoxycarbonyl and $R^{11}$ is lower ($C_{1-8}$) alkyl, aryl (e.g. phenyl, and the like), cyano, carbamoyl, or alkoxycarbonyl and $R^{12}$ is di-alkyl-substituted amino (e.g. dimethylamino, diethylamino, morpholino, piperidino, piperazino, and the like)].

Examples of aryl groups for $R^2$ include phenyl, naphthyl and the like. Said aryl groups may be optionally substituted with 1 to 3 substituents selected from halogen (e.g. fluorine, chlorine, bromine, and the like), lower ($C_{1-4}$) alkyl (e.g. methyl, ethyl, and the like), nitro and the like at an optional position on the ring.

Examples of aralkyl groups for $R^2$ include phenyl-lower ($C_{1-4}$) alkyl such as benzyl, phenethyl, and the like. Said aralkyl groups may be optionally substituted with 1 to 3 substituents selected from halogen (e.g. fluorine, chlorine, bromine, and the like), nitro, lower ($C_{1-4}$) alkyl (e.g. methyl, ethyl, and the like), and the like at an optional position on the ring.

The hydrocarbon residues for $R^3$ include acyclic hydrocarbon residues, aryl and aralkyl groups. Examples of such acyclic hydrocarbon residues for $R^3$ include alkyl of 1 to about 8 carbon atoms and alkenyl of 2 to about 8 carbon atoms. The acyclic hydrocarbon residues for $R^3$ may be optionally substituted with nitrile, carbamoyl, aryl (e.g. phenyl, and the like), hydroxyl, carboxyl, ester (e.g. $C_{2-5}$ alkanoyloxy, $C_{1-4}$ alkoxycarbonyl, and the like), optionally substituted amino (e.g. amino, lower ($C_{1-4}$) alkylamino, di-lower ($C_{1-4}$) alkylamino, $C_{2-5}$ alkanoylamino, and the like), or the like. Examples of such alkyl and alkenyl for $R^3$ include methyl, ethyl, propyl, isopropyl, allyl, butyl, isobutyl, sec-butyl, t-butyl, butenyl, pentyl, isopentyl, pentenyl, hexyl, isohexyl, hexenyl, cyclohexyl, and the like. Examples of aryl groups for $R^3$ include phenyl, and the like. Said aryl groups may be optionally substituted with 1 to 3 substituents selected from halogen (e.g. fluorine, chlorine, bromine, and the like), lower ($C_{1-4}$) alkyl (e.g. methyl, ethyl, and the like), nitro and the like at an optional position on the ring. Examples of aralkyl groups for $R^3$ include phenyl-lower ($C_{1-4}$) alkyl such as benzyl, phenethyl, and the like. Said aralkyl groups may be optionally substituted with 1 to 3 substituents selected from halogen (e.g. fluorine, chlorine, bromine, and the like), nitro, lower ($C_{1-4}$) alkyl (e.g. methyl, ethyl, and the like), and the like at an optional position on the ring. $R^3$ may be in the ortho, meta or para position.

The spacers having one atomic length for X include —O—, —S—,

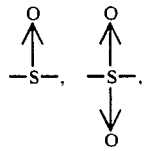

an imino group having the formula:

wherein $R^9$ is hydrogen, an acyl group of 1 to about 4 carbon atoms derived from fatty acid (e.g. formyl, acetyl, propionyl, and the like), or alkyl of 1 to about 4 carbon atoms (e.g. methyl, ethyl, propyl, and the like), and the like.

$R^4$ represents hydrogen, halogen (e.g. chlorine, bromine, and the like) or nitro, and may be in the ortho or meta position.

Examples of residues capable of forming an anion and residues convertible into the anion for $R^5$ include carboxyl, lower ($C_{1-4}$) alkoxycarbonyl, cyano, tetrazolyl, trifluoromethanesulfonic amide (—NHSO$_2$CF$_3$), phosphoric acid, sulfonic acid, and the like. These groups are optionally protected with an optionally substituted lower ($C_{1-4}$) alkyl group (e.g. lower ($C_{2-6}$) alkanoyloxy-lower ($C_{1-4}$) alkyl, lower ($C_{1-6}$) alkoxy-lower ($C_{1-4}$) alkyl, lower ($C_{1-6}$) alkoxycarbonyloxy-lower ($C_{1-4}$) alkyl, etc.). Such residues may include those which are capable of forming anions either chemically or under biological and/or physiological conditions, and may be in the ortho, meta or para position. The compounds wherein $R^5$ is a residue capable of forming an anion or convertible thereinto chemically (e.g. by oxidation, reduction or hydrolysis) (e.g. cyano and the like), are useful as synthetic intermediates.

Y shows that the adjacent phenylene group is bonded to the phenyl group directly or through a spacer whose atomic chain is 2 or less. As the spacer, any one can be exemplified, so long as it is a divalent chain in which the number of atoms constituting the straight chain is 1 or 2, and it may have a side chain. Examples of such spacers include lower ($C_{1-4}$) alkylene, —C(=O)—, —O—, —S—, —NH—, —C(=O)—NH—, —O—CH$_2$—, —S—CH$_2$—, —CH=CH—, etc.

A preferred embodiment of the invention is a compound of the formula (I'):

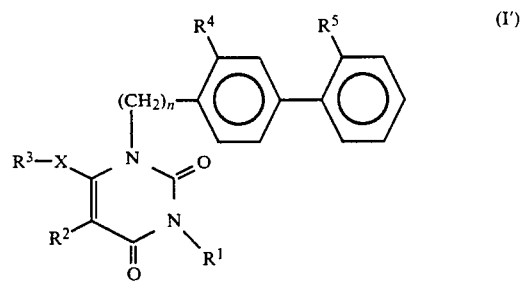

wherein $R^1$ is lower ($C_{2-5}$) alkyl, which may be optionally substituted with carboxyl, lower ($C_{1-4}$) alkoxycarbonyl or substituted carbamoyl; $R^2$ is hydrogen; $R^3$ is lower ($C_{2-5}$) alkyl, which may be optionally substituted with lower ($C_{1-4}$) alkoxycarbonyl; X is a direct bond, —S—, —S(O)—, —S(O)$_2$—, —O—, —NH— or —N(-lower ($C_{2-5}$) alkyl)-; $R^4$ is hydrogen, halogen or nitro (inter alia hydrogen); and $R^5$ is carboxyl or tetrazolyl (inter alia tetrazolyl); and the pharmaceutically acceptable salts thereof.

The compounds (I) of the present invention may be prepared by several reaction schemes, as illustrated below for a preferred compound.

Scheme A

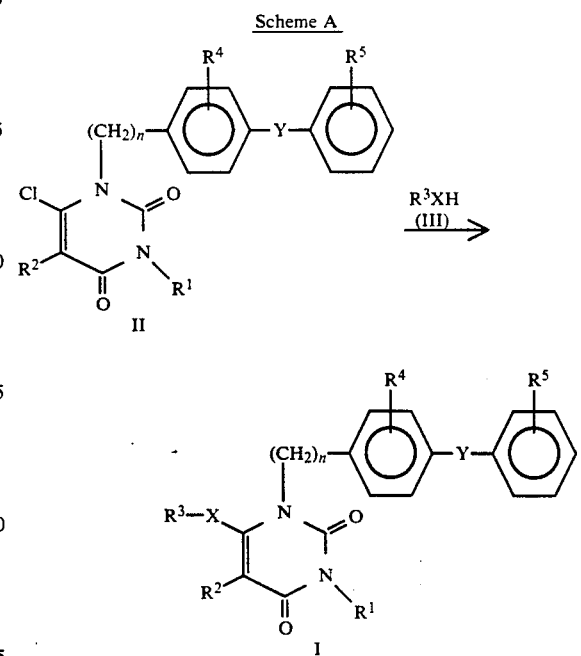

wherein $R^1$, $R^2$, $R^3$, $R^4$, $R^5$, X, Y and n have the abovedefined meanings.

Scheme B

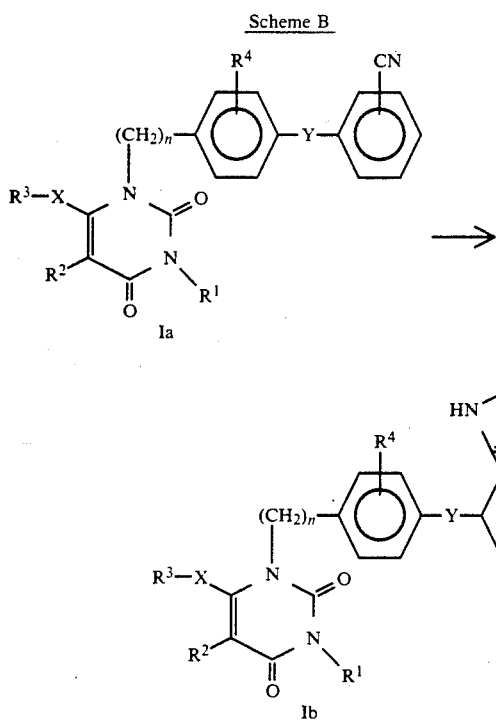

wherein each group is of the same meaning as defined above.

Scheme C

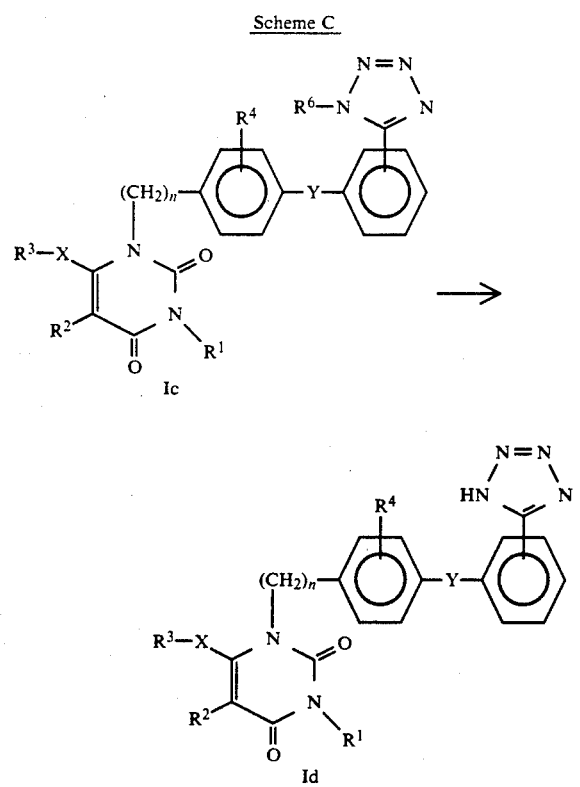

wherein $R^1$, $R^2$, $R^3$, $R^4$, X and n have the above-defined meanings and $R^6$ is optionally substituted lower ($C_{1-4}$) alkyl.

Scheme D

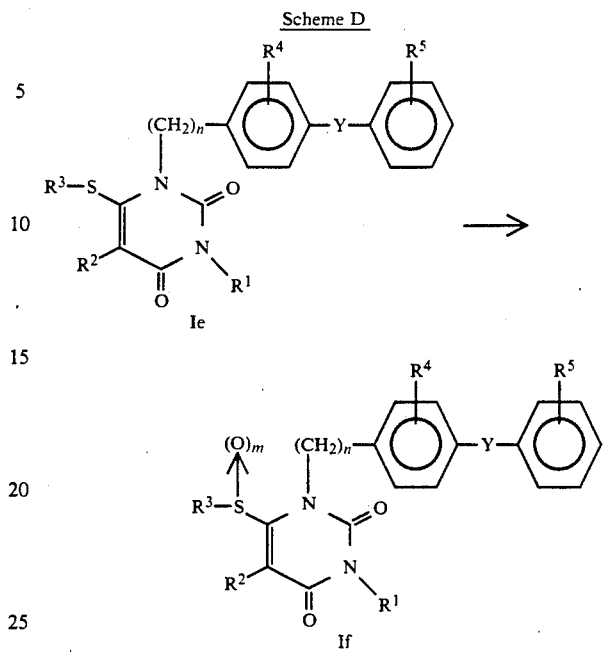

wherein $R^1$, $R^2$, $R^3$, $R^4$, $R^5$, Y and n have the above-defined meanings and m is an integer of 1 or 2.

In the reaction scheme A, the chloride (II) is reacted with the nucleophilic reagent (III) to form the substituted product (I). One molar portion of the compound (II) is employed with about 1 to about 3 moles of the nucleophilic reagent (III). The reaction can be carried out in the presence of a suitable base depending on which nucleophilic reagent is used. The reaction is conventionally conducted in solvents such as alcohols (e.g. methanol, ethanol, etc), ketones (e.g. acetone, methylethylketone), acetonitrile, ethers (e.g. tetrahydrofuran, dioxane), dimethylformamide, dimethylacetamide, dimethylsulfoxide, and the like. The nucleophilic reagent used can also be employed dually as a solvent. Examples of such nucleophilic reagents include alcohols (e.g. methanol, ethanol, etc), amines (e.g. optionally substituted primary or secondary alkylamine such as methylamine, ethylamine, dimethylamine, etc, optionally substituted arylamine such as aniline, p-methoxyaniline, etc, optionally substituted aralkylamine such as benzylamine, p-chlorobenzylamine, etc), mercaptans (e.g. alkylmercaptan such as methylmercaptan, ethylmercaptan, propylmercaptan, etc, phenylmercaptan, benzylmercaptan, etc). The reaction can be carried out in the co-existence of a suitable base such as sodium hydride, potassium t-butoxide, potassium carbonate, sodium carbonate, and the like depending on which nucleophilic reagent is used. The reaction conditions may vary depending on the combination of the nucleophilic reagent (III) and the base. The reaction is usually conducted at temperatures ranging from ice-cooling to the boiling point of the solvent for about 1 to about 40 hours and preferably at room temperature to 100° C. for about 1 to about 10 hours.

The cyano substituent on the benzene of the compounds (Ia) is reacted with various azides to form the tetrazole compounds (Ib) as illustrated in Scheme B. One molar portion of the compound (Ia) is employed with about 1 to about 3 moles of the azide. The reaction is conventionally conducted in solvents such as dimethylformamide, dimethylacetamide, toluene, benzene, and the like.

Examples of such azides include trialkyl-tin azide, triphenyl-tin azide, hydrogen azide, and the like. In the case where the organo-tin azide compound is employed, the reaction is carried out in toluene or benzene by heating under a reflux for a period of from about 10 to about 30 hours. When the hydrogen azide is used, 2 moles of sodium azide and ammonium chloride per compound (Ia) are employed and the reaction is conducted in dimethylformamide at a temperature ranging from about 100° C. to about 130° C. for 1 to 3 days. During this reaction, it is preferable to facilitate working by adding an appropriate amount of sodium azide and ammonium chloride.

The protective group ($R^6$) on the tetrazole compound (Ic) is deprotected in the presence of an acid or alkali to form the tetrazole compound (Ic) as illustrated in Scheme C. As the acid, use is made of an organic acid such as acetic acid and p-toluene-sulfonic acid, and a mineral acid such as hydrochloric acid and sulfuric acid. As the alkali, use is made of an aqueous solution of ammonium hydroxide, potassium carbonate, sodium carbonate, caustic soda, caustic potash and the like. Suitable solvents which can be used include conventional organic solvents such as alcohols (e.g. methanol, ethanol, etc.), ethers (e.g. tetrahydrofuran, dioxane, etc.), acetonitrile, and the like, acetic acid, water, and the like, and mixed solvents thereof. One molar portion of the tetrazole compound (Ic) which is dissolved in the above-mentioned solvent is employed with a catalytic amount to about 3 moles of the acid or alkali. The reaction may be conducted at a temperature in the range from room temperature to about 50° C. for a period from about 1 to about 10 hours. The reaction is preferably conducted in the alcohol containing 1N hydrochloric acid at approximate room temperature for a period from about 3 to about 5 hours.

The compound (Ie) is reacted with an oxidizing agent in an organic solvent to form the compound (If) as illustrated in Scheme D. Suitable solvents which can be used include halogenated hydrocarbons such as dichloromethane, chloroform, dichloroethane, etc., ethers such as ethyl ether, tetrahydrofuran, dioxane, etc., ketones such as acetone, methylethylketone, etc. Among them, the halogenated hydrocarbon is most preferred. Oxidizing agents include organic peracids such as m-chloroperbenzoic acid, etc., N-halocarboxamides such as N-bromosuccinimide, etc., periodic acid, and the like. Among them, m-chloroperbenzoic acid is most preferred. Generally, the oxidizing agent is employed in an slightly excess amount when compared to the compound (Ie). Advantageously, the reaction is carried out by adding m-chloroperbenzoic acid portionwise to a stirred solution of the compound (Ie) in methylene chloride under ice-cooling and then allowing them to stir at a temperature in the range from about ice-cooled temperature to about room temperature for a period from about 3 to about 10 hours.

The compounds (I) thus produced via the reaction processes as depicted in Schemes A, B, C and D can be isolated and purified from the reaction mixture according to conventional methods such as, for example, evaporation of solvents, extraction by water or organic solvents, concentration, neutralization, recrystallization, distillation, column chromatography and the like, to obtain a crystalline or oily product.

The compounds (I) of the present invention can be used in the form of salts derived from pharmaceutically or physiologically acceptable acids or bases. These salts include but are not limited to the following: salts with inorganic acids such as hydrochloric acid, sulphuric acid, nitric acid, phosphoric acid and, as the case may be, such organic acids as acetic acid, oxalic acid, succinic acid, maleic acid. Other salts include salts with alkali metals or alkaline earth metals, such as sodium, potassium, calcium or magnesium or with organic bases.

The starting materials (II) can also be easily prepared from the compounds (V) as illustrated in Scheme E.

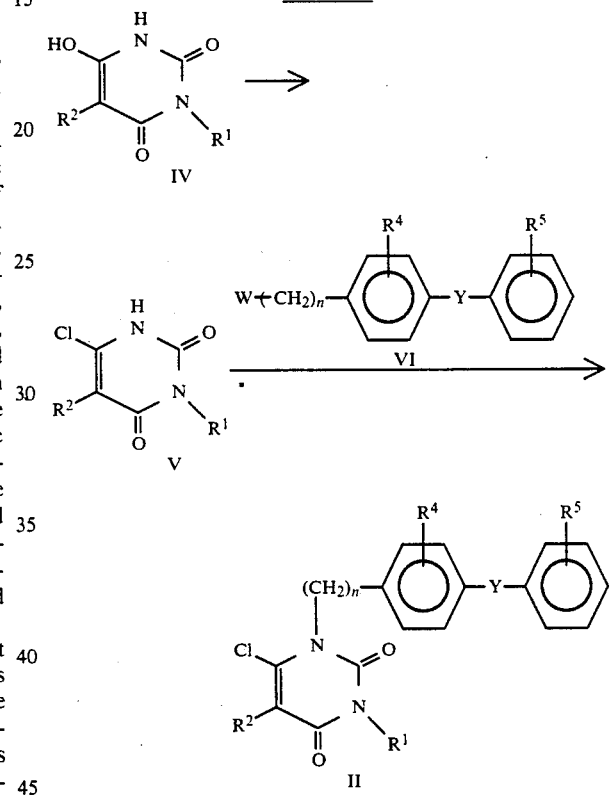

wherein each group has the above-defined meaning, and W is halogen.

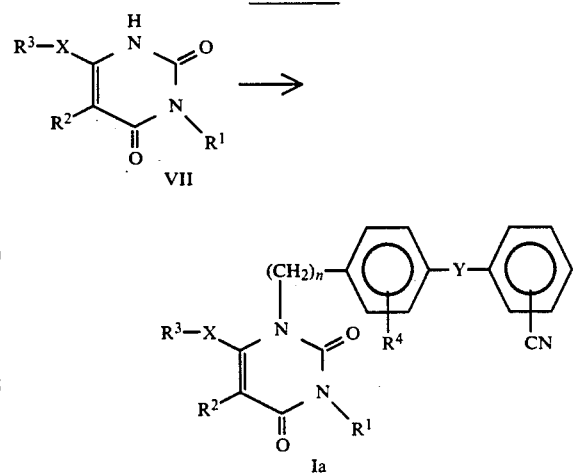

wherein $R^1$, $R^2$, $R^3$, $R^4$, X, Y and n have the above-defined meanings.

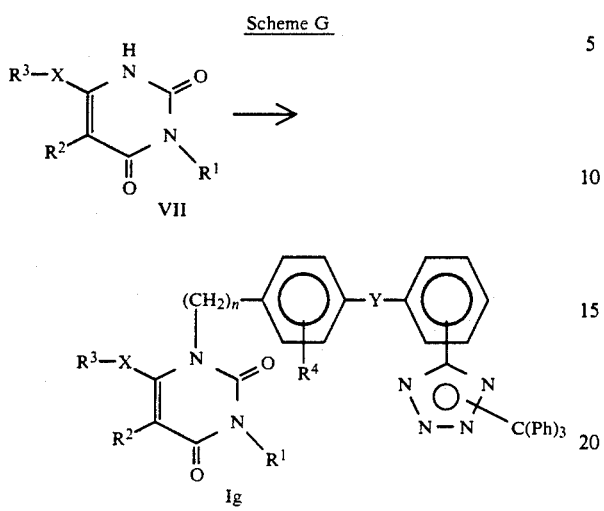

Scheme G wherein $R^1$, $R^2$, $R^3$, $R^4$, X, Y and n have the above-defined meanings.

The starting materials (IV), (V) and (VII) may be prepared by or according to methods described in, for example, (1) Chem. Ber., 95, 1597, (1962),
(2) Ann. Chem., 691, 142, (1966),
(3) G. W. Anderson, I. F. Halverstadt, W. H. Miller and R. O. Roblin, J. Am. Chem. Soc., 67, 2197 (1945),
(4) E. Coats, W. R. Glave and C. Hansch, J. Med. Chem., 13, 913 (1970),
(5) F. H. S. Curd, D. N. Richardson and F. L. Rose, J. Chem. Soc., 343 (1946),
(6) T. Kinoshita, N. Nakahata, A. Kouchi and S. Furukawa, Chem. Pharm. Bull., 36, 3887 (1988),
(7) J. P. Horwitz and A. J. Tomson, J. Org. Chem., 26, 3392 (1961),
(8) R. Kaul and B. Hempel, Arzneim.-Forsch., 32, 722 (1982),
(9) J. A. Hendry and R. F. Homer, J. Chem. Soc., 328 (1952),
(10) S. B. Greenbaum and W. L. Holmes, J. Am. Chem. Soc., 76, 2899 (1954),
(11) K. Tanaka, T. Kimura, T. Okada, X. Chen and F. Yoneda, Chem. Pharm. Bull., 35, 1397 (1987),
(12) K. Edo, T. Sakamoto and H. Yamanaka, Chem. Pharm. Bull., 26, 3843 (1978),
(13) R. Kaul, G. Kiefer and B. Hempel, Arzneim.-Forsch., 32, 610 (1982),
(14) G. Kiefer, R. Kaul, K. Keppeler and B. Hempel, Arch. Pharm., 315, 444 (1982), and
(15) Y. Ikoma, S. Higuchi and Y. Naoi, Japanese Patent Laid Open No. 83072/1989.

The compounds (IV), (V) and (VII) are easily reacted with a suitable halide compound (VI) such as, for example, 4'-chloromethyl-2-cyanobiphenyl, 4'-bromomethyl-2-cyanobiphenyl, methyl 4'-chloromethylbiphenyl-2-carboxylate, methyl 4'-bromomethylbiphenyl-2-carboxylate, N-triphenylmethyl-5-[2-(4'-chloromethylbiphenylyl)]tetrazole, N-triphenylmethyl-5-[2-(4'-bromomethylbiphenylyl)]tetrazole, etc. in a polar solvent such as, for example, dimethylformamide, etc. in the presence of potassium carbonate, sodium carbonate or the like at a temperature in the range from about 50° C. to about 100° C. for a period from about 5 to about 20 hours to form the compound (II), (Ia) or (Ig).

The compound (VI) wherein n is 1 (the compounds (VIa)) is commercially available or easily prepared by halogenomethylation according to methods described in known literatures such as, for example,

(16) J. R. E. Hoover, A. W. Chow, R. J. Stedman, N. M. Hall, H. S. Greenberg, M. M. Dolan and R. J. Feriauto, J. Med. Chem., 7, 245 (1964),
(17) R. J. Stedman, J. R. E. Hoover, A. W. Chow, M. M. Dolan, N. M. Hall and R. J. Feriauto, J. Med. Chem., 7, 251 (1964),
(18) H. Gilman and R. D. Gorsich, J. Am. Chem. Soc., 78, 2217 (1956), and
(19) M. Orchin and E. Oscar Woolfolk, J. Am. Chem. Soc., 67, 122 (1945).

Scheme H

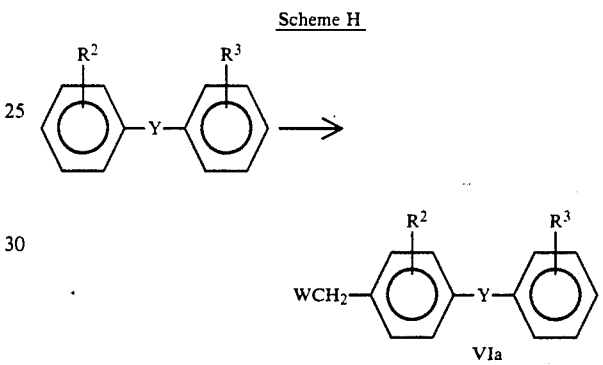

wherein each group has the above-defined meaning.

The compounds (VI) wherein n is 2 (the compounds (VIb)) can also be easily prepared from the compounds (VIa) as illustrated in Scheme I.

Scheme I

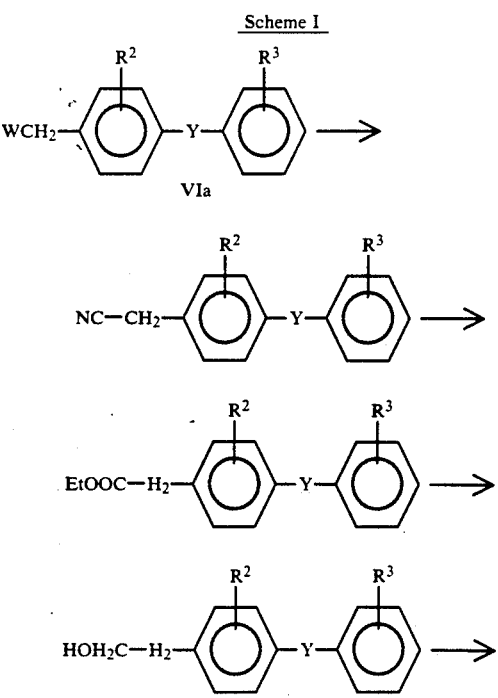

-continued
Scheme 1

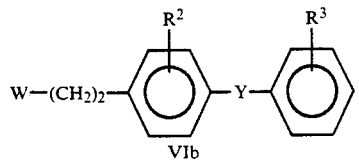

wherein each group has the above-defined meaning.

The compounds (I) and salts thereof according to the present invention inhibit strongly vasoconstriction and hypertension derived by angiotensin II and therefore possess potent anti-hypertensive activity in animals, more specifically mammal animals (e.g. humans, dogs, rabbits, rats, etc.). Further, the compounds (I) and salts thereof according to the present invention are of quite low toxicity and useful in treating not only hypertension but also circulatory system diseases such as heart diseases, strokes and the like.

For therapeutic use, the compounds (I) and salts thereof can be administered as pharmaceutical compositions (e.g. powders, granules, tablets, pills, capsules, injections, solutions and the like) comprising at least one such compound alone or in admixture with pharmaceutically acceptable carriers, excipients and/or diluents. The pharmaceutical compositions can be formulated in accordance with a conventional method.

Specific dose levels for any particular patient will be employed depending upon a variety of factors including the activity of specific compounds employed, the age, body weight, general health, sex, diet, time of administration, route of administration, rate of excretion, drug combination, and the severity of the particular disease undergoing therapy. When used for treating adult essential hypertension, the active ingredient will preferably be administered in an appropriate amount, for example, selected from the range of about 10 mg to 100 mg a day orally and from the range of about 5 mg to 50 mg a day intravenously. The active ingredient will preferably be administered in equal doses two or three times a day.

The foregoing is merely illustrative of the invention and is not intended to limit the invention to the disclosed compounds. Variations and changes which are obvious to one skilled in the art are intended to be within the scope and nature of the invention.

EXAMPLE

The invention is further illustrated but in no way limited by the following pharmaceutical examples, working examples, reference examples and experimental examples.

In the specification of the present application, examples of the abbreviations used are given below. Me: Methyl, Et: Ethyl, Pr: Propyl, Bu: Butyl, Ph: Phenyl, DMF: Dimethylformamide.

PHARMACEUTICAL EXAMPLES

The compounds (I) of the present invention are employed, for example, when used as agents for treating circulatory system diseases such as hypertension, heart diseases, strokes and the like, in the following formulations.

| 1. Capsule | |
|---|---|
| (1) 3-Propyl-6-propylthio-1-[[2'-(1H-tetrazol-5-yl)biphenyl-4-yl]-methyl]pyrimidine-2,4(1H, 3H)-dione | 10 mg |
| (2) Lactose | 90 mg |
| (3) Microcrystalline cellulose | 70 mg |
| (4) Magnesium stearate | 10 mg |
| One capsule | 180 mg |

The ingredients (1), (2), and (3) and a half of the ingredient (4) were blended together and granulated. To this mixture was added the remaining half of the ingredient (4) and distributed into gelatine capsules.

| 2. Tablet | |
|---|---|
| (1) 3-Butyl-6-propylthio-1-[[2'-(1H-tetrazol-5-yl)biphenyl-4-yl]-methyl]pyrimidine-2,4(1H, 3H)-dione | 10 mg |
| (2) Lactose | 35 mg |
| (3) Maize starch | 150 mg |
| (4) Microcrystalline cellulose | 30 mg |
| (5) Magnesium stearate | 5 mg |
| One tablet | 230 mg |

Two third each of the ingredients (1), (2), (3) and (4) and a half of the ingredient (5) were blended together and granulated. To these granules were added the remaining ingredients (4) and (5) and then compressed to form tablets.

| 3. Injection | |
|---|---|
| (1) 3-Propyl-6-propylthio-1-[[2'-(1H-tetrazol-5-yl)biphenyl-4-yl]-methyl]pyrimidine-2,4(1H, 3H)-dione | 10 mg |
| (2) Inositol | 100 mg |
| (3) Benzyl alcohol | 20 mg |
| One ampule | 130 mg |

The ingredients (1), (2) and (3) were dissolved in distilled water for injection to a total volume of two ml and distributed into ampules. Total processes were carried out under sterile conditions.

WORKING EXAMPLE 1

6-Methylthio-3-propyl-1-[[2'-(1H-tetrazol-5-yl)biphenyl-4-yl]methyl]pyrimidine -2,4(1H,3H)-dione A mixture of 6-chloro-3-propyl-1-[[2'-(N-trityltetrazol-5-yl)biphenyl-4-yl]methyl]pyrimidine-2,4(1H,3H)-dione (0.6 g), methylmercaptan (15%, 0.51 g) and potassium carbonate (0.13 g) in acetonitrile (10 ml) was heated under reflux for 6 hours with stirring. The insoluble material was removed from the reaction mixture by filtration and the filtrate was concentrated to dryness. The resulting residue was dissolved in methanol (15 ml) and then 1N hydrochloric acid (1 ml) was added to the solution, followed by stirring at room temperature for 3 hours. The reaction mixture was concentrated to dryness and then the residue was extracted with methylene chloride-water. The organic layer was washed with water, dried, and evaporated to dryness. The resulting residue was purified by column chromatography on silica gel to give colorless powders (0.22 g, 54%).

| Elemental Analysis for $C_{22}H_{22}N_6O_2S \cdot H_2O$ | | | |
|---|---|---|---|
| | C (%) | H (%) | N (%) |
| Calcd: | C, 58.39; | H, 5.35; | N, 18.57 |
| Found: | C, 58.27; | H, 5.01; | N, 18.42. |

$^1$H-NMR (200 MHz, CDCl$_3$) δ: 0.92(3H, t), 1.55–1.73(2H, m), 2.43(3H, s), 3.87(2H, t), 5.19(2H, s), 5.52(1H, s), 7.14–7.64(7H, m), 8.08(1H, d).

WORKING EXAMPLE 2

6-Ethylthio-3-propyl-1-[[2'-(1H-tetrazol-5-yl)biphenyl-4-yl]methyl]pyrimidine-2,4(1H,3H)-dione A mixture of 6-chloro-3-propyl-1-[[2'-(N-trityltetrazol-5-yl)biphenyl-4-yl]methyl]pyrimidine-2,4(1H,3H)-dione (0.6 g), ethylmercaptan (0.08 ml) and potassium carbonate (0.25 g) in acetonitrile (10 ml) was heated at 70° C. for 2 hours with stirring. The insoluble material was removed from the reaction mixture by filtration and the filtrate was concentrated to dryness. The resulting residue was dissolved in methanol (15 ml) and then 1N hydrochloric acid (2 ml) was added to the solution, followed by stirring at room temperature for 21 hours. The reaction mixture was concentrated to dryness and then the residue was extracted with methylene chloride-water. The organic layer was washed with water, dried, and evaporated to dryness. The resulting residue was purified by column chromatography on silica gel to give colorless powders (0.2 g, 48%).

| Elemental Analysis for $C_{23}H_{24}N_6O_2S \cdot \frac{1}{2} H_2O$ | | | |
|---|---|---|---|
| | C (%) | H (%) | N (%) |
| Calcd: | C, 60.38; | H, 5.51; | N, 18.37 |
| Found: | C, 60.37; | H, 5.30; | N, 18.10 |

$^1$H-NMR (200 MHz, CDCl$_3$) δ: 0.92(3H, t), 1.41(3H, t), 1.56–1.75(2H, m), 2.94(2H, q), 3.87(2H, t), 5.20(2H, s), 5.57(1H, s), 7.17–7.64(7H, m), 8.12–8.17(1H, m).

WORKING EXAMPLE 3

3-Propyl-6-propylthio-1-[[2'-(1H-tetrazol-5-yl)biphenyl-4-yl]methyl]pyrimidine-2,4(1H,3H)-dione A mixture of 6-chloro-3-propyl-1-[[2'-(N-trityltetrazol-5-yl)biphenyl-4-yl]methyl]pyrimidine-2,4(1H,3H)-dione (1 g), propylmercaptan (0.17 ml) and potassium carbonate (0.25 g) in acetonitrile (10 ml) was heated under reflux for 3 hours with stirring. The insoluble material was removed from the reaction mixture by filtration and the filtrate was concentrated to dryness. The resulting residue was dissolved in methanol (30 ml) and then 1N hydrochloric acid (3.0 ml) was added to the solution, followed by stirring at room temperature for 5 hours. The reaction mixture was concentrated to dryness and then the residue was extracted with methylene chloride-water. The organic layer was washed with water, dried, and evaporated to dryness. The resulting residue was purified by column chromatography on silica gel to give colorless powders (0.4 g, 56%).

| Elemental Analysis for $C_{24}H_{26}N_6O_2S \cdot \frac{1}{2} H_2O$ | | | |
|---|---|---|---|
| | C (%) | H (%) | N (%) |
| Calcd: | C, 61.13; | H, 5.77; | N, 17.82 |

| Elemental Analysis for $C_{24}H_{26}N_6O_2S \cdot \frac{1}{2} H_2O$ -continued | | | |
|---|---|---|---|
| | C (%) | H (%) | N (%) |
| Found: | C, 61.32; | H, 5.70; | N, 17.48 |

$^1$H-NMR (200 MHz, CDCl$_3$) δ: 0.90(3H, t), 1.05(3H, t), 1.52–1.86(4H, m), 2.88(2H, t), 3.83(2H, t), 5.18(2H, s), 5.57(1H, s), 7.23(4H, dd), 7.42–7.65(3H, m), 8.04(1H, d).

WORKING EXAMPLE 4

6-Butylthio-3-propyl-1-[[2'-(1H-tetrazol-5-yl)biphenyl-4-yl]methyl]pyrimidine-2,4(1H,3H)-dione A mixture of 6-chloro-3-propyl-1-[[2'-(N-trityltetrazol-5-yl)biphenyl-4-yl]methyl]pyrimidine-2,4(1H,3H)-dione (0.5 g), butylmercaptan (0.1 ml) and potassium carbonate (0.13 g) in acetonitrile (10 ml) was heated under reflux for 3 hours with stirring. The insoluble material was removed from the reaction mixture by filtration and the filtrate was concentrated to dryness. The resulting residue was dissolved in methanol (15 ml) and then 1N hydrochloric acid (1.5 ml) was added to the solution, followed by stirring at room temperature for 3 hours. The reaction mixture was concentrated to dryness and then the residue was extracted with methylene chloride-water. The organic layer was washed with water, dried, and evaporated to dryness. The resulting residue was purified by column chromatography on silica gel to give colorless powders (0.2 g, 55%).

| Elemental Analysis for $C_{25}H_{28}N_6O_2S \cdot \frac{1}{2} H_2O$ | | | |
|---|---|---|---|
| | C (%) | H (%) | N (%) |
| Calcd: | C, 62.77; | H, 5.94; | N, 17.57 |
| Found: | C, 62.66; | H, 5.94; | N, 17.36 |

$^1$H-NMR (200 MHz, CDCl$_3$) δ: 0.92(3H, t), 0.96(3H, t), 1.38–1.79(6H, m), 2.91(2H, t), 3.86(2H, t), 5.21(2H, s), 5.58(1H, s), 7.28(4H, dd), 7.41–7.65(3H, m), 8.12–8.17(1H, m).

WORKING EXAMPLE 5

6-Cyclohexylthio-3-propyl-1-[[2'-(1H-tetrazol-5-yl)biphenyl-4-yl]methyl]pyrimidine-2,4(1H,3H)-dione A mixture of 6-chloro-3-propyl-1-[[2'-(N-trityltetrazol-5-yl)biphenyl-4-yl]methyl]pyrimidine-2,4(1H,3H)-dione (0.5 g), cyclohexylmercaptan (0.12 ml) and potassium carbonate (0.13 g) in acetonitrile (10 ml) was heated under reflux for 5 hours with stirring. The reaction mixture was allowed to cool and the precipitate was removed by filtration. The filtrate was concentrated to dryness. The resulting residue was dissolved in methanol (15 ml) and then 1N hydrochloric acid (1.5 ml) was added to the solution, followed by stirring at room temperature for 3 hours. The reaction mixture was concentrated to dryness and then the residue was extracted with methylene chloride-water. The organic layer was washed with water, dried, and evaporated to dryness. The resulting residue was purified by column chromatography on silica gel to give colorless amorphous powders (0.2 g, 52%).

| Elemental Analysis for $C_{27}H_{30}N_6O_2S \cdot \frac{1}{2} H_2O$ | | | |
|---|---|---|---|
| | C (%) | H (%) | N (%) |
| Calcd: | C, 63.38; | H, 6.11; | N, 16.43 |

| Elemental Analysis for $C_{27}H_{30}N_6O_2S.\frac{1}{2} H_2O$ | | | |
|---|---|---|---|
| | C (%) | H (%) | N (%) |
| Found: | C, 63.61; | H, 6.08; | N, 16.30 |

$^1$H-NMR (200 MHz, CDCl$_3$) δ: 0.93(3H, t), 1.25–1.88(10H, m), 2.08–2.18(2H, m), 3.19–3.31(1H, m), 3.87 (2H, t), 5.23(2H, s), 5.67(1H, s), 7.29(4H, dd), 7.41–7.67(3H, m), 8.16–8.22(1H, m).

WORKING EXAMPLE 6

6-Pentylthio-3-propyl-1-[[2'-(1H-tetrazol-5-yl)biphenyl-4-yl]methyl]pyrimidine-2,4(1H,3H)-dione A mixture of 6-chloro-3-propyl-1-[[2'-(N-trityltetrazol-5-yl)biphenyl-4-yl]methyl]pyrimidine-2,4(1H,3H)-dione (0.5 g), pentylmercaptan (0.12 ml) and potassium carbonate (0.13 g) in acetonitrile (10 ml) was heated under reflux for 4 hours with stirring. The reaction mixture was allowed to cool and the precipitate was removed by filtration. The filtrate was concentrated to dryness. The resulting residue was dissolved in methanol (15 ml) and then 1N hydrochloric acid (1.5 ml) was added to the solution, followed by stirring at room temperature for 2 hours. The reaction mixture was concentrated to dryness and then the residue was extracted with methylene chloride-water. The organic layer was washed with water, dried, and evaporated to dryness. The resulting residue was purified by column chromatography on silica gel to give colorless amorphous powders (0.16 g, 43%).

| Elemental Analysis for $C_{26}H_{30}N_6O_2S.\frac{1}{2} H_2O$ | | | |
|---|---|---|---|
| | C (%) | H (%) | N (%) |
| Calcd: | C, 62.50; | H, 6.25; | N, 16.82 |
| Found: | C, 62.59; | H, 6.19; | N, 16.70 |

$^1$H-NMR (200 MHz, CDCl$_3$) δ: 0.91(3H, t), 0.92(3H, t), 1.28–1.51(4H, m), 1.56–1.81(4H, m), 2.90(2H, t), 3.86(2H, t), 5.21(2H, s), 5.58(1H, s), 7.28(4H, dd), 7.40–7.66(3H, m), 8.13–8.18(1H, m).

WORKING EXAMPLE 7

6-Benzylthio-3-propyl-1-[[2'-(1H-tetrazol-5-yl)biphenyl-4-yl]methyl]pyrimidine-2,4(1H,3H)-dione A mixture of 6-chloro-3-propyl-1-[[2'-(N-trityltetrazol-5-yl)biphenyl-4-yl]methyl]pyrimidine-2,4(1H,3H)-dione (0.5 g), benzylmercaptan (0.11 ml) and potassium carbonate (0.13 g) in acetonitrile (10 ml) was heated under reflux for 4 hours with stirring. The reaction mixture was allowed to cool and the precipitate was removed by filtration. The filtrate was concentrated to dryness. The resulting residue was dissolved in methanol (15 ml) and then 1N hydrochloric acid (1.5 ml) was added to the solution, followed by stirring at room temperature for 5 hours. The reaction mixture was concentrated to dryness and then the residue was extracted with methylene chloride-water. The organic layer was washed with water, dried, and evaporated to dryness. The resulting residue was purified by column chromatography on silica gel to give colorless amorphous powders (0.26 g, 67%).

| Elemental Analysis for $C_{28}H_{26}N_6O_2S.\frac{1}{2} H_2O$ | | | |
|---|---|---|---|
| | C (%) | H (%) | N (%) |
| Calcd: | C, 64.72; | H, 5.24; | N, 16.17 |
| Found: | C, 64.88; | H, 5.14; | N, 16.01 |

$^1$H-NMR (200 MHz, CDCl$_3$) δ: 0.91(3H, t), 1.54–1.73(2H, m), 3.85(2H, t), 4.13(2H, s), 5.19(2H, s), 5.67(1H, s), 7.25(4H, dd), 7.36(5H, s), 7.39–7.65(3H, m), 8.13(1H, dd).

WORKING EXAMPLE 8

6-Ethoxy-3-propyl-1-[[2'-(1H-tetrazol-5-yl)biphenyl-4-yl]methyl]pyrimidine-2,4(1H,3H)-dione 6-Chloro-3-propyl-1-[[2'-(N-trityltetrazol-5-yl)biphenyl-4-yl]methyl]pyrimidine-2,4(1H,3H)-dione (0.8 g) was dissolved in a solution of sodium metal (69 mg) in ethanol (10 mL) and the mixture was heated under reflux for 14 hours with stirring. The reaction mixture was concentrated to dryness and the resulting residue was dissolved in methylene chloride-water. The solution was acidified with 1N hydrochloric acid (1.5 ml), extracted and the organic layer was separated. The organic layer was washed with water, dried, and evaporated to dryness. The resulting residue was purified by column chromatography on silica gel to give white amorphous powders (0.36 g, 69%). M.p. 108°–119° C.

| Elemental Analysis for $C_{23}H_{24}N_6O_3.7/10\ H_2O$ | | | |
|---|---|---|---|
| | C (%) | H (%) | N (%) |
| Calcd: | C, 62.07; | H, 5.75; | N, 18.88 |
| Found: | C, 62.21; | H, 5.48; | N, 18.85 |

$^1$H-NMR (200 MHz, CDCl$_3$) δ: 0.90(3H, t), 1.41(3H, t), 1.51–1.70(2H, m), 3.82(2H, t), 4.07(2H, q), 5.05(2H, s), 5.12(1H, s), 7.21(4H, dd), 7.39–7.63(3H, m), 8.03(1H, d).

WORKING EXAMPLE 9

3-Butyl-6-propylthio-1-[[2'-(1H-tetrazol-5-yl)biphenyl-4-yl]methyl]pyrimidine-2,4(1H,3H)-dione 3-Butyl-6-propylthio-1-[[2'-(N-trityltetrazol-5-yl)biphenyl-4-yl]methyl]pyrimidine-2,4(1H,3H)-dione (0.45 g) was dissolved in a mixed solution of methanol (10 ml) and 1N hydrochloric acid (1 ml) and the solution was stirred at room temperature for 4 hours. The reaction mixture was concentrated to dryness and the resulting residue was extracted with methylene chloride-water. The organic layer was washed with water, dried, and evaporated to dryness. The resulting residue was purified by column chromatography on silica gel to give colorless amorphous powders (0.25 g, 84%).

$^1$H-NMR (200 MHz, CDCl$_3$) δ: 0.93(3H, t), 1.06(3H, t), 1.25–1.45(2H, m), 1.53–1.69(2H, m), 1.70–1.88 (2H, m), 2.89(2H, t), 3.90(2H, t), 5.22(2H, s), 5.58(1H, s), 7.28(4H, dd), 7.41–7.65(3H, m), 8.15(1H, dd).

WORKING EXAMPLE 10

3-Butyl-6-phenylthio-1-[[2'-(1H-tetrazol-5-yl)biphenyl-4-yl]methyl]pyrimidine-2,4(1H,3H)-dione A mixture of 3-butyl-6-chloro-1-[[2'-(N-trityltetrazol-5-yl)biphenyl-4-yl]methyl]pyrimidine-2,4(1H,3H)-dione (0.52 g), thiophenol (0.1 ml) and potassium carbonate (0.15 g) in acetonitrile (10 ml) was heated under reflux for 4 hours with stirring. The reaction mixture was allowed to cool and the insoluble material was removed from the reaction mixture by filtration. The filtrate was concentrated to dryness. The resulting residue was dissolved in methanol (15 ml) and 1N hydrochloric acid (1 ml) and the mixture stirred at room temperature for 4 hours. The reaction mixture was concentrated to dryness and the residue was extracted with methylene chloride-water. The organic layer was washed with water, dried, and evaporated to dryness. The resulting residue was purified by column chromatography on silica gel to give colorless amorphous powders (0.27 g, 69%).

$^1$H-NMR (200 MHz, CDCl$_3$) δ: 0.91(3H, t), 1.25–1.42(2H, m), 1.51–1.66(2H, m), 3.88(2H, t), 5.06(1H, s), 5.32(2H, s), 7.34(4H, dd), 7.43–7.66(8H, m), 8.17(1H, dd).

WORKING EXAMPLE 11

6-Ethoxycarbonylmethylthio-3-ethyl-1-[[2'-(1H-tetrazol-5-yl)biphenyl-4-yl]methyl]pyrimidine-2,4(1H,3H)-dione A mixture of 6-chloro-3-ethyl-1-[[2'-(N-trityltetrazol-5-yl)biphenyl-4-yl]methyl]pyrimidine-2,4(1H,3H)-dione (0.6 g), ethyl thioglycollate (0.13 ml) and potassium carbonate (0.19 g) in acetonitrile (10 ml) was heated under reflux for 10 hours with stirring. The reaction mixture was allowed to cool and the precipitate was removed by filtration. The filtrate was concentrated to dryness. The resulting residue was dissolved in methanol (15 ml) and 1N hydrochloric acid (1.5 ml), followed by stirring at room temperature for 7 hours. The reaction mixture was concentrated to dryness and then the residue was extracted with methylene chloride-water. The organic layer was washed with water, dried, and evaporated to dryness. The resulting residue was purified by column chromatography on silica gel to give pale yellow amorphous powders (0.15 g, 33%).

$^1$H-NMR (200 MHz, CDCl$_3$) δ: 1.24(3H, t), 1.28(3H, t), 3.73(2H, s), 4.02(2H, q), 4.21(2H, q), 5.29(2H, s), 5.56(1H, s), 7.25(4H, dd), 7.43–7.65(3H, m), 8.12(1H, dd).

WORKING EXAMPLE 12

3-Benzyl-6-tert-butylthio-1-[[2'-(1H-tetrazol-5-yl)biphenyl-4-yl]methyl]pyrimidine-2,4(1H,3H)-dione A mixture of 3-benzyl-6-chloro-1-[[2'-(N-trityltetrazol-5-yl)biphenyl-4-yl]methyl]pyrimidine-2,4(1H,3H)-dione (0.5 g), tert-butylmercaptan (0.1 ml) and potassium carbonate (0.14 g) in acetonitrile (10 ml) was heated under reflux for 8 hours with stirring. The reaction mixture was allowed to cool and the precipitate was removed by filtration. The filtrate was concentrated to dryness. The resulting residue was dissolved in methanol (15 ml) and 1N hydrochloric acid (1 ml) and the mixture was stirred at room temperature for 4 hours. The reaction mixture was concentrated to dryness and then the residue was extracted with methylene chloride-water. The organic layer was washed with water, dried, and evaporated to dryness. The resulting residue was purified by column chromatography on silica gel to give pale yellow amorphous powders (0.2 g, 54%).

$^1$H-NMR (200 MHz, CDCl$_3$) δ: 1.49(9H, s), 5.10(2H, s), 5.35(2H, s), 6.10(1H, s), 7.23(4H, dd), 7.26–7.66(8H, m), 8.16(1H, d).

WORKING EXAMPLE 13

5-Phenyl-3-propyl-6-propylthio-1-[[2'-(1H-tetrazol-5-yl)biphenyl-4-yl]methyl]pyrimidine-2,4(1H,3H)-dione A mixture of 6-chloro-5-phenyl-3-propyl-1-[[2'-(N-trityltetrazol-5-yl)biphenyl-4-yl]methyl]pyrimidine-2,4(1H,3H)-dione (0.5 g), propylmercaptan (0.08 ml) and potassium carbonate (0.14 g) in acetonitrile (10 ml) was heated under reflux for 4 hours with stirring. The reaction mixture was allowed to cool and the precipitate was removed by filtration. The filtrate was concentrated to dryness. The resulting residue was dissolved in methanol (15 ml) and 1N hydrochloric acid (1 ml) and the mixture was stirred at room temperature for 4 hours. The reaction mixture was concentrated to dryness and then the residue was extracted with methylene chloride-water. The organic layer was washed with water, dried, and evaporated to dryness. The resulting residue was purified by column chromatography on silica gel to give colorless amorphous powders (0.26 g, 72%).

$^1$H-NMR (200 MHz, CDCl$_3$) δ: 0.69(3H, t), 0.93(3H, t), 1.22–1.40(2H, m), 1.59–1.79(2H, m), 2.18(2H, t), 3.93(2H, t), 5.55(2H, s), 7.30(4H, dd), 7.37(5H, s), 7.39–7.66(3H, m), 8.13(1H, dd).

WORKING EXAMPLE 14

3-Propyl-6-propylamino-1-[[2'-(1H-tetrazol-5-yl)biphenyl-4-yl]methyl]pyrimidine-2,4(1H,3H)-dione A solution of 6-chloro-3-propyl-1-[[2'-(N-trityltetrazol-5-yl)biphenyl-4-yl]methyl]pyrimidine-2,4(1H,3H)-dione (1.0 g) and propylamine (0.19 g) in ethanol (20 ml) was heated under reflux for 18 hours with stirring. The reaction mixture was concentrated to dryness and then the residue was extracted with methylene chloride-dilute hydrochloric acid. The organic layer was washed with water, and evaporated to dryness. The resulting residue was purified by column chromatography on silica gel to give pale yellow powders (0.58 g, 83%).

| Elemental Analysis for C$_{24}$H$_{27}$N$_7$O$_2$·H$_2$O | | |
|---|---|---|
| C (%) | H (%) | N (%) |
| Calcd: C, 62.19; | H, 6.31; | N, 21.15 |
| Found: C, 62.29; | H, 5.93; | N, 21.06 |

$^1$H-NMR (200 MHz, CDCl$_3$) δ: 0.77(3H, t), 0.87(3H, t), 1.39–1.70(4H, m), 2.91(2H, q), 3.84(2H, t), 4.84(2H, s), 5.11(2H, s), 7.06(4H, s), 7.35–7.59(3H, m), 7.83(1H, d).

WORKING EXAMPLE 15

6-(N-Methylbutylamino)-3-propyl-1-[[2'-(1H-tetrazol-5-yl)biphenyl-4-yl]methyl]pyrimidine-2,4(1H,3H)-dione A solution of 6-chloro-3-propyl-1-[[2'-(N-trityltetrazol-5-yl)biphenyl-4-yl]methyl]pyrimidine-2,4(1H,3H)-dione (0.5 g) and N-methylbutylamine (0.2 g) in ethanol (10 ml) was heated under reflux for 8 hours. The reaction mixture was concentrated to dryness and then the residue was extracted with methylene chloride-dilute hydrochloric acid. The organic layer was washed with water, and evaporated to dryness. The resulting residue was purified by column chromatography on silica gel to give pale yellow amorphous powders (0.26 g, 73%).

¹H-NMR (200 MHz, CDCl₃) δ: 0.86(6H, t), 1.12–1.30(2H, m), 1.47–1.68(4H, m), 2.67(3H, s), 2.88(2H, t), 3.79(2H, t), 5.06(2H, s), 5.30(1H, s), 7.16(4H, s), 7.38–7.63(3H, m), 8.06(1H, dd).

WORKING EXAMPLE 16

3-Propyl-6-propylsulfinyl-1-[[2'-(N-trityltetrazol-5-yl)biphenyl-4-yl]methyl]pyrimidine-2,4(1H,3H)-dione To a solution of 3-propyl-6-propylthio-1-[[2'-(N-trityltetrazol-5-yl)biphenyl-4-yl]methyl]pyrimidine-2,4(1H,3H)-dione (0.6 g) in dichloromethane (10 ml) was added m-chloroperbenzoic acid (0.16 g) and the mixture was stirred at room temperature for 16 hours. The reaction mixture was washed with an aqueous sodium bicarbonate solution and water, and evaporated to dryness. The resulting residue was purified by column chromatography on silica gel to give colorless powders (0.27 g, 44%).

¹H-NMR (200 MHz, CDCl₃) δ: 0.85(3H, t), 0.98(3H, t), 1.60–1.78(4H, m), 2.26–2.42(2H, m), 3.96(2H, t), 5.00(2H, dd), 6.42(1H, s), 6.92–7.52(22H, m), 7.89–7.94(1H, m).

WORKING EXAMPLE 17

5-Chloro-6-(1-methylpropylthio)-3-propyl-1-[[2'-(1H-tetrazol-5-yl)biphenyl-4-yl]methyl]pyrimidine-2,4(1H,3H)-dione A mixture of 5,6-dichloro-3-propyl-1-[[2'-(N-trityltetrazol-5-yl)biphenyl-4-yl]methyl]pyrimidine-2,4(1H,3H)-dione (0.22 g), sec-butylmercaptan (0.04 g) and potassium carbonate (0.09 g) in acetonitrile (5 ml) was heated under reflux for 4 hours. The reaction mixture was concentrated to dryness. The resulting residue was dissolved in methanol (15 ml) and 1N hydrochloric acid (1.5 ml) and the mixture was stirred at room temperature for 1 hour. The reaction mixture was concentrated to dryness and then the residue was extracted with methylene chloride-water. The organic layer was washed with water, dried, and evaporated to dryness. The resulting residue was purified by column chromatography on silica gel to give yellow amorphous powders (90 mg, 56%).

¹H-NMR (200 MHz, CDCl₃) δ: 0.94(3H, t), 1.02(3H, t), 1.28(3H, d), 1.57–1.79(4H, m), 3.59–3.74(1H, m), 3.97(2H, t), 5.54(2H, dd), 7.26(4H, dd), 7.39–7.66(3H, m), 8.18(1H, dd).

WORKING EXAMPLE 18

3-Propyl-6-propyloxy-1-[[2'-(1H-tetrazol-5-yl)biphenyl-4-yl]methyl]pyrimidine-2,4(1H,3H)-dione To a solution of sodium (0.09 g) in propanol was added 6-chloro-3-propyl-1-[[2'-(N-trityltetrazol-5-yl)biphenyl-4-yl]methyl]pyrimidine-2,4(1H,3H)-dione (0.8 g) was added and the mixture was heated under reflux for 14 hours. The reaction mixture was concentrated to dryness. The resulting residue was dissolved in methylene chloride-water. The aqueous layer was acidified with 1N hydrochloric acid and extracted with methylene chloride. The organic layer was washed with water, dried, and evaporated to dryness. The resulting residue was purified by column chromatography on silica gel to give colorless amorphous powders (0.38 g, 69%).

Elemental Analysis for C₂₄H₂₆N₆O₃·½ H₂O

|        | C (%)   | H (%)   | N (%)   |
|--------|---------|---------|---------|
| Calcd: | C, 63.28; | H, 5.97; | N, 18.45 |
| Found: | C, 63.32; | H, 5.85; | N, 18.31 |

¹H-NMR (200 MHz, CDCl₃) δ: 0.91(3H, t), 0.98(3H, t), 1.52–1.71(2H, m), 1.73–1.90(2H, m), 3.83(2H, t), 3.97(2H, t), 5.08(2H, s), 5.12(1H, s), 7.25(4H, dd), 7.39–7.64(3H, m), 8.07(1H, dd).

WORKING EXAMPLE 19

3-Propyl-6-propylthio-1-[[2'-(1H-tetrazol-5-yl)biphenyl-4-yl]methyl]pyrimidine-2,4(1H,3H)-dione A mixture of 1-(2'-cyanobiphenyl-4-yl)methyl-3-propyl-6-propylthiopyrimidine-2,4(1H,3H)-dione (0.77 g), sodium azide (1.8 g) and ammonium chloride (1.48 g) in dimethylformamide (10 ml) was heated at 115° C. for 84 hours. The reaction mixture was diluted with methylene chloride and then the precipitate was filtered. The filtrate was concentrated to dryness in vacuo. The resulting residue was extracted with methylene chloride water. The organic layer was washed with water, dried, and evaporated to dryness. The resulting residue was purified by column chromatography on silica gel to give yellow amorphous powders (0.41 g, 46%).

¹H-NMR (200 MHz, CDCl₃) δ: 0.91(3H, t), 1.06(3H, t), 1.54–1.72(2H, m), 1.68–1.88(2H, m), 2.88(2H, t), 3.84(2H, t), 5.19(2H, s), 5.57(1H, s), 7.24(4H, dd), 7.41–7.65(3H, m), 8.04–8.09(1H, m).

WORKING EXAMPLE 20

3-Propyl-6-propylsulfonyl-1-[[2'-(1H-tetrazol-5-yl)biphenyl-4-yl]methyl]pyrimidine-2,4(1H,3H)-dione A solution of 3-propyl-6-propylthio-1-[[2'-(N-triphenylmethyltetrazol-5-yl)biphenyl-4-yl]methyl]pyrimidine-2,4(1H,3H)-dione (0.6 g) in methanol (15 ml) and 1N hydrochloric acid (1.5 ml) was stirred at room temperature for 14 hours. The solution was evaporated to dryness and the residue was dissolved in chloroform. The solution was washed with water, dried, and evaporated to dryness. The resulting syrup was dissolved in methylene chloride (5 ml) and to the solution was added m-chloroperbenzoic acid (0.37 g). The reaction mixture was stirred at room temperature for 20 hours and then it was concentrated to dryness. The resulting syrup was purified by column chromatography on silica gel to give pale brown powders (0.08 g, 20%).

M.p. 128°–135° C.

¹H-NMR (200 MHz, CDCl₃) δ: 0.92(6H, t), 1.56–1.83(4H, m), 2.92(2H, t), 3.90(2H, t), 5.50(2H, s), 5.50(2H, s), 6.61(1H, s), 7.19(4H, dd), 7.37–7.64(3H, m), 7.96(1H, d).

WORKING EXAMPLE 21

1-[[2'-(N-methyltetrazol-5-yl)biphenyl-4-yl]methyl]-3-propyl-6-propyloxypyrimidine-2,4(1H,3H)-dione A mixture of 3-propyl-6-propyloxy-1-[[2'-(1H-tetrazol-5-yl)biphenyl-4-yl]methyl]pyrimidine-2,4(1H,3H)-dione (0.1 g), methyl iodide (50 mg) and sodium bicarbonate (25 mg) in DMF (5 ml) was stirred at room temperature for 2 hours. The reaction mixture was concentrated to dryness and the residue was dissolved in CHCl₃-water. The chloroform layer was dried and evaporated in vacuo to give a syrup. The syrup was column-chromatographed on silica gel to give a colorless syrup (90 mg, 86%).

| Elemental Analysis for $C_{25}H_{28}N_6O_3 \cdot 0.8 H_2O$ | | | |
|---|---|---|---|
| | C (%) | H (%) | N (%) |
| Calcd: | C, 63.22; | H, 6.28; | N, 17.69 |
| Found: | C, 63.18; | H, 5.99; | N, 17.55 |

WORKING EXAMPLE 22

1-[[2'-(N-pivaloyloxymethyltetrazol-5-yl)biphenyl-4-yl]methyl]-3-propyl-6-propyloxypyrimidine-2,4(1H,3H)-dione A mixture of 3-propyl-6-propyloxy-1-[[2'-(1H-tetrazol-5-yl)biphenyl-4-yl]methyl]pyrimidine-2,4(1H,3H)-dione (0.1 g), pivaloyloxymethyl iodide (90 mg) and sodium bicarbonate (35 mg) in DMF (2 ml) was stirred at room temperature for 20 hours. The reaction mixture was evaporated to dryness and the residue was dissolved in chloroform-water. The chloroform layer was dried and evaporated in vacuo to give a syrup. The syrup was column-chromatographed on silica gel to give a colorless syrup (0.1 g, 81%).

| Elemental Analysis for $C_{30}H_{36}N_6O_5$ | | | |
|---|---|---|---|
| | C (%) | H (%) | N (%) |
| Calcd: | C, 64.27; | H, 6.47; | N, 14.99 |
| Found: | C, 64.39; | H, 6.21; | N, 14.70 |

The following compounds (Working Examples 23-29) were prepared according to the procedure for Working Example 1.

TABLE 1a

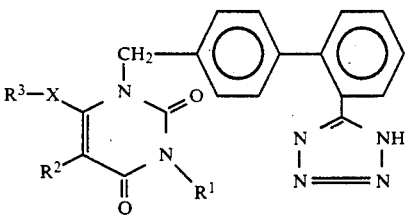

| Working Example No. | $R^1$ | $R^2$ | $-X-R^3$ | MP. (°C.) | Yield (%) |
|---|---|---|---|---|---|
| 23 | Et | H | Pr | powder | 46 |
| 24 | Pr | H | Me | powder | 29 |
| 25 | Pr | H | Pr | powder | 59 |
| 26 | Bu | H | Pr | powder | 37 |
| 27 | —CH$_2$COOMe | H | Pr | powder | 96 |
| 28 | —CH$_2$COOEt | H | Pr | powder | 23 |
| 29 | —CH$_2$(CH$_2$)$_3$COOMe | H | Pr | powder | 69 |

TABLE 1b

| Working Example No. | $^1$H-NMR (200MHz, CDCl$_3$) α | E. Anal. (Calcd/Found) C (%), H (%), O (%) |
|---|---|---|
| 23 | 0.99, 1.20(each 3H, t), 1.52-1.71 (2H, m), 2.41(2H, t), 3.98(2H, t), 5.11(2H, s), 5.66(1H, s), 7.10-7.22 (4H, m), 7.39-7.6(3H, m), 8.03-8.08 (1H, m) | $C_{23}H_{24}N_6O_2 \cdot 0.7H_2O$ 64.38; 5.67; 19.59 64.60; 5.69; 19.51 |
| 24 | 0.92(3H, t), 1.55-1.76(2H, m), 2.20 (3H, s), 3.90(2H, t), 5.11(2H, s), 5.64(1H, s), 7.18(4H, s), 7.38-7.63 (3H, m), 8.05-8.11(1H, m) | $C_{22}H_{22}N_6O_2 \cdot 0.8 H_2O$ 63.39; 5.71; 20.16 63.57; 5.43; 19.73 |
| 25 | 0.92, 1.00(each 3H, t), 1.54-1.74 (4H, m), 2.42, 3.89(each 2H, t), 5.12(2H, s), 5.66(1H, s), 7.18 (4H, dd), 7.39-7.64(3H, m), 8.07-8.12 (1H, m) | $C_{24}H_{26}N_6O_2 \cdot 0.2 H_2O$ 66.40; 6.13; 19.36 66.24; 6.04; 19.15 |
| 26 | 0.92, 1.00(each 3H, t), 1.26-1.45 (2H, m), 1.52-1.70(4H, m), 2.41, 3.92 (each 2H, t), 5.11(2H, s), 5.66(1H, s), 7.16(4H, dd), 7.39-7.63(3H, m), 8.05 (1H, d) | $C_{25}H_{28}N_6O_2 \cdot 0.4 H_2O$ 66.47; 6.43; 18.60 66.61; 6.29; 18.27 |
| 27 | 1.02(3H, t), 1.55-1.74(2H, m), 2.46 (2H, t), 3.74(3H, s), 4.72(2H, s), 5.13(2H, s), 5.74(1H, s). 7.19(2H, s), 7.39-7.65(3H, m), 8.06-o.11(1H, m) | $C_{24}H_{24}N_6O_4 \cdot 0.8 H_2O$ 60.70; 5.43; 17.70 60.62; 5.25; 17.68 |
| 28 | 1.00, 1.25(each 3H, t), 1.54-1.72 (2H, m), 2.42(2H, t), 4.18(2H, q), 4.70, 5.09(each 2H, s), 5.72(1H, s), 7.12 (4H, s), 7.36-7.42(1H, m), 7.47-7.62 (2H, m), 8.04(1H, d) | $C_{25}H_{26}N_6O_4 \cdot 0.6 H_2O$ 61.87; 5.65; 17.32 61.94; 5.49; 16.92 |
| 29 | 1.02(3H, t), 1.50-1.74(6H, m), 2.36, 2.46, 3.97(each 2H, t), 3.59(3H, s), 5.09(2H, s), 5.68(1H, s), 7.13, 7.19 (each 2H, d), 7.40-7.62(3H, m), 8.04 (1H, dd) | $C_{27}H_{30}N_6O_4 \cdot 0.5 H_2O$ 63.39; 6.11; 16.43 63.39; 5.86; 16.53 |

The following compounds (Working Examples 30-35) were prepared according to the procedure for Working Example 19.

TABLE 2a (Structure: biphenyl-tetrazole with pyrimidinedione bearing N-CH₂-biphenyl, R¹ on N, R³ on ring)

| Working Example No. | R¹ | R³ | MP. (°C.) | Yield (%) |
|---|---|---|---|---|
| 30 | —CH₂CON⟨N-Ph⟩ (piperazine) | Pr | powder | 64 |
| 31 | —CH₂CONHPh | Pr | powder | 78 |
| 32 | —CH₂CONH—C₆H₄—COOMe | Pr | powder | 54 |
| 33 | —CH₂CONHCH₂Ph | Pr | 178–180 | 31 |
| 34 | —CH₂CONHCH₂—(2-pyridyl) | Pr | powder | 64 |
| 35 | —CH₂CONHCH₂—C₆H₄—OMe | Pr | 162–165 | 31 |

TABLE 2b

| Working Example No. | ¹H-NMR (200MHz, CDCl₃) α | E. Anal. (Calcd/Found) C (%), H (%), O (%) |
|---|---|---|
| 30 | 0.99(3H, t), 1.51–1.70(2H, m), 2.43 (2H, t), 3.08–3.27(4H, m), 3.61–3.73 (4H, m), 4.82(2H, s), 5.03(2H, s), 5.69 (1H, s), 6.87–6.94(3H, m), 7.04(2H, d), 7.10(2H, d), 7.22–7.59(5H, m), 7.89 (1H, d) | C₃₃H₃₄N₈O₃·H₂O<br>65.12; 5.96; 18.41<br>65.16; 5.60; 18.41 |
| 31 | 0.90(3H, t), 1.39–1.58(2H, m), 2.28 (2H, t), 4.71, 4.95(each 2H, s), 5.64 (1H, s), 6.90–7.51(12H, m), 7.82–7.91 (1H, m) | C₂₉H₂₇N₇O₃·H₂O<br>64.55; 5.42; 18.17<br>64.72; 5.00; 17.90 |
| 32 | 0.99(3H, t), 1.52–1.71(2H, m), 2.45 (2H, t), 3.87(3H, s), 4.81(2H, s), 5.08(2H, s), 5.74(1H, s), 7.01–7.18 (5H, m), 7.33–7.60(5H, m), 7.89–8.08 (2H, m), 8.55(1H, d) | |
| 33 | 0.97(3H, t), 1.48–1.66(2H, m), 2.40 (2H, t), 4.32(2H, d), 4.58, 5.02(each 2H, s), 5.69(1H, s), 6.80(1H, br), 7.05(4H, s), 7.15–7.58(8H, m), 7.90 (1H, d) | C₃₀H₂₉N₇O₃·0.5 CH₂Cl₂<br>63.37; 5.23; 16.96<br>63.47; 5.06; 16.75 |
| 34 | 0.93(3H, t), 1.45–1.61(2H, m), 2.35 (2H, t), 4.39, 4.67, 4.95(each 2H, s), 5.67(1H, s), 6.88–7.08(5H, m), 7.18–7.59 (5H, m), 7.75–7.88(2H, m), 8.22–8.30 (1H, m) | C₂₉H₂₈N₈O₃·0.5 CH₃OH·0.4 CH₂Cl₂<br>61.22; 5.29; 19.10<br>61.28; 5.01; 19.00 |
| 35 | 1.01(3H, t), 1.55–1.75(2H, m), 2.46 (2H, t), 3.82(3H, s), 4.40(2H, d), 4.56, 5.07(each 2H, s), 5.70(1H, s), 6.54 (1H, t), 6.86(2H, t), 7.07–7.30(6H, m), 7.37–7.43(1H, m), 7.49–7.62(2H, m), 7.99(1H, dd) | C₃₁H₃₁N₇O₄·0.4H₂O<br>65.00; 5.60; 17.12<br>65.13; 5.38; 17.08 |

WORKING EXAMPLE 36

2,4-Dioxo-6-propyl-1-[[2'-(1H-tetrazol-5-yl)biphenyl-4-yl]methyl]-1,2,3,4-tetrahydropyrimidine-3-acetic acid A mixture of methyl 2,4-dioxo-6-propyl-1-[[2'-(1H-tetrazol-5-yl)biphenyl-4-yl]methyl]-1,2,3,4-tetrahydropyrimidine-3-acetate (0.25 g) in methanol (10 ml) and 1N sodium hydroxide (1.5 ml) was heated under reflux for 16 hours. The reaction solution was evaporated to dryness and the residue was dissolved in water. The solution was acidified with 1N hydrochloric acid to give a crystalline product (0.19 g, 79%).

| Elemental Analysis for $C_{23}H_{22}N_6O_4 \cdot 3/5\ H_2O$ | | | |
|---|---|---|---|
| | C (%) | H (%) | N (%) |
| Calcd: | C, 60.41; | H, 5.11; | N, 18.38 |
| Found: | C, 60.45; | H, 5.13; | N, 18.55. |

$^1$H-NMR (200 MHz, DMSO-d$_6$) δ: 0.87(3H, t), 1.40-1.58(2H, m), 2.42(2H, t), 4.50(2H, s), 5.13(2H, s), 5.69(1H, s), 7.06-7.16(4H, m), 7.51-7.71(4H, m).

REFERENCE EXAMPLE 1

2-(4-Chloromethylphenyl)benzonitrile

To vigorously stirred 2-phenylbenzonitrile (68.1 g) under ice-cooling was added titanium tetrachloride (432 g) dropwise for 30 minutes. The precipitated crystals were pulverized and then chloromethyl-methyl ether (61 g) was added dropwise for 20 minutes with stirring under ice-cooling. After stirring at 60° C. for 2 hours, additional chloromethyl-methyl ether (15.3 g) was added and the mixture was stirred for an additional hour. To the reaction mixture was added ethyl acetate (200 ml) dropwise with stirring under ice-cooling. Then ice was added until hydrogen chloride gas development ceased and iced water (400 ml) was added before stirring for a while. The precipitated crystals were filtered and dried. The filtrate was extracted with ethyl acetate, washed with water, and concentrated to dryness in vacuo. The resulting residue was purified by column chromatography on silica gel to give crystals which were combined with the previously obtained crystal and recrystallized from methanol to yield pale yellow prisms (41.8 g, 48%).

M.p. 125°-126° C.

$^1$H-NMR (CDCl$_3$, 90 MHz) δ: 4.64(2H, s), 7.30-7.65(7H, m), 7.75(1H, dd).

IR (KBr)cm$^{-1}$: 2220, 1475, 1445, 1275, 835, 820, 760, 730, 690, 670.

REFERENCE EXAMPLE 2

6-Chloro-1-(2'-cyanobiphenyl-4-yl)methyl-3-propyl-pyrimidine-2,4(1H,3H)-dione A mixture of 6-chloro-3-propylpyrimidine-2,4(1H,3H)-dione (3 g), 4-chloromethyl-2'-cyanobiphenyl (4.76 g) and potassium carbonate (2.64 g) in DMF (50 ml) was stirred at room temperature for 3 hours and then at 60° C. for 2 hours. The reaction mixture was concentrated to dryness in vacuo and then the residue was dissolved in methylene chloride. The insoluble material was removed from the reaction mixture by filtration and the filtrate was concentrated to dryness. The resulting residue was purified by column chromatography on silica gel to give colorless crystals (5.9 g, 98%).

M.p. 146°-147° C.

$^1$H-NMR (200 MHz, CDCl$_3$) δ: 0.94(3H, t), 1.47-1.91(2H, m), 3.91(2H, t), 5.33(2H, s), 5.94(1H, s), 7.33-7.84(8H, m).

REFERENCE EXAMPLE 3

6-Chloro-3-propyl-1-[[2'-(N-trityltetrazol-5-yl)biphenyl-4-yl]methyl]pyrimidine-2,4(1H,3H)-dione A mixture of 6-chloro-3-propylpyrimidine-2,4(1H,3H)-dione (1.7 g), N-triphenylmethyl-5-[2-(4'-bromomethylbiphenyl)]tetrazole (5.52 g) and K$_2$CO$_3$ (1.5 g) in DMF (50 ml) was stirred at room temperature for 25 hours. The reaction mixture was concentrated to dryness and then the residue was extracted with methylene chloride-water. The organic layer was washed with water, dried, and evaporated to dryness. The resulting residue was purified by column chromatography on silica gel to give white powders (4 g, 67%).

$^1$H-NMR (200 MHz, CDCl$_3$) δ: 0.94(3H, t), 1.58-1.75(2H, m), 3.89(2H, t), 5.14(2H, s), 5.88(1H, s), 6.87-6.93(6H, m), 7.07(16H, m), 7.91-7.97(1H, m).

REFERENCE EXAMPLE 4

3-Benzyl-6-chloro-1-[[2'-(N-trityltetrazol-5-yl)biphenyl-4-yl]methyl]pyrimidine-2,4(1H,3H)-dione A mixture of 3-benzyl-6-chloropyrimidine-2,4(1H,3H)-dione (0.5 g), 4-bromomethyl-2'-(N-trityltetrazol-5-yl)biphenyl (1.24 g) and potassium carbonate (0.36 g) in DMF (20 ml) was stirred at room temperature for 24 hours. The reaction mixture was concentrated to dryness in vacuo and then the residue was dissolved in methylene chloride. The insoluble material was removed from the reaction mixture by filtration and the filtrate was concentrated to dryness. The resulting residue was purified by column chromatography on silica gel to give colorless amorphous powders (0.8 g, 53%).

$^1$H-NMR (200 MHz, CDCl$_3$) δ: 5.10(2H, s), 5.13(2H, s), 5.91(1H, s), 6.86-6.92(6H, m), 7.08(4H, dd), 7.19-7.51(17H, m), 7.92-7.97(1H, m).

REFERENCE EXAMPLE 5

6-Chloro-5-phenyl-3-propyl-1-[[2'-(N-trityltetrazol-5-yl)biphenyl-4-yl]methyl]-pyrimidine-2,4(1H,3H)-dione A mixture of 6-chloro-5-phenyl-3-propyl-pyrimidine-2,4(1H,3H)-dione (0.5 g), 4-bromomethyl-2'-(N-trityltetrazol-5yl)biphenyl (1.11 g) and potassium carbonate (0.32 g) in DMF (20 ml) was stirred at room temperature for 22 hours. The reaction mixture was concentrated to dryness in vacuo and then the residue was dissolved in methylene chloride. The insoluble material was removed from the reaction mixture by filtration and the filtrate was concentrated to dryness. The resulting residue was purified by column chromatography on silica gel to give colorless amorphous powders (0.67 g, 48%).

$^1$H-NMR (200 MHz, CDCl$_3$) δ: 0.98(3H, t), 1.65-1.83(2H, m), 3.99(2H, t), 5.26(2H, s), 6.85-6.92(6H, m), 7.12-7.52(21H, m), 7.93-7.98(1H, m).

REFERENCE EXAMPLE 6

6-Chloro-3-ethyl-1-[[2'-(N-trityltetrazol-5-yl)biphenyl-4-yl]methyl]pyrimidine-2,4(1H,3H)-dione A mixture of 6-chloro-3-ethylpyrimidine-2,4(1H,3H)-dione (0.5 g), 4-bromomethyl-2'-(N-trityltetrazol-5-yl)biphenyl (1.68 g) and potassium carbonate (0.48 g) in DMF (20 ml) was stirred at room temperature for 20 hours. The reaction mixture was concentrated to dryness in vacuo and then the residue was dissolved in methylene chloride. The insoluble material was removed from the reaction mixture by filtration and the filtrate was concentrated to dryness. The resulting residue was purified by column chromatography on silica gel to give colorless amorphous powders (1.3 g, 70%).

$^1$H-NMR (200 MHz, CDCl$_3$) δ: 1.23(3H, t), 4.00(2H, q), 5.15(2H, s), 5.89(1H, s), 6.87-6.93(6H, m), 7.12(4H, s), 7.16-7.52(12H, m), 7.92-7.98(1H, m).

REFERENCE EXAMPLE 7

3-Butyl-6-chloro-1-[[2'-(N-trityltetrazol-5-yl)biphenyl-4-yl]methyl]pyrimidine-2,4(1H,3H)-dione A mixture of 3-butyl-6-chloropyrimidine-2,4(1H,3H)-dione (1 g), 4-bromomethyl-2'-(N-trityltetrazol-5-yl)biphenyl (3.02 g) and potassium carbonate (0.82 g) in DMF (50 ml) was stirred at 60° C. for 4 hours. The reaction mixture was concentrated to dryness in vacuo and then the residue was dissolved in methylene chloride. The insoluble material was removed from the reaction mixture by filtration and the filtrate was concentrated to dryness. The resulting residue was purified by column chromatography on silica gel and recrystallized from ethyl acetate-hexane to give colorless prisms (1.97 g, 59%).

$^1$H-NMR (200 MHz, CDCl$_3$) δ: 0.94(3H, t), 1.29-1.46(2H, m), 1.56-1.70(2H, m), 3.92(2H, t), 5.14(2H, s). 5.88(1H, s), 6.87-6.93(6H, m), 7.07-7.53(16H, m), 7.92-7.96(1H, m).

REFERENCE EXAMPLE 8

3-Butyl-6-propylthio-1-[[2'-(N-trityltetrazol-5-yl)biphenyl-4-yl]methyl]pyrimidine-2,4(1H,3H)-dione A mixture of 3-butyl-6-chloro-1-[[2'-(N-trityltetrazol-5-yl)biphenyl-4-yl]methyl]pyrimidine-2,4(1H,3H)-dione (1.4 g), propylmercaptan (0.24 ml) and potassium carbonate (0.35 g) in acetonitrile (25 ml) was heated under reflux for 3 hours. The reaction mixture was allowed to cool and the precipitate was removed by filtration. The filtrate was concentrated to dryness. The resulting residue was purified by column chromatography on silica gel to give colorless amorphous powders (1 g, 68%).

$^1$H-NMR (200 MHz, CDCl$_3$) δ: 0.94(3H, t), 1.00(3H, t), 1.29-1.46(2H, m), 1.57-1.78(4H, m), 2.77(2H, t), 3.92(2H, t), 5.09(2H, s), 5.51(1H, s), 6.89-6.95(6H, m), 7.10(4H, s), 7.21-7.52(12H, m), 7.86-7.91(1H, m).

REFERENCE EXAMPLE 9

1-(2'-Cyanobiphenyl-4-yl)methyl-3-propyl-6-propylthiopyrimidine-2,4(1H,3H)-dione A mixture of 6-chloro-1-(2'-cyanobiphenyl-4-yl)methyl-3-propylpyrimidine-2,4(1H,3H)-dione (0.7 g), propylmercaptan (0.2 ml) and potassium carbonate (0.51 g) in acetonitrile (12 ml) was stirred at room temperature for 3 hours. The reaction mixture was concentrated to dryness and then the residue was extracted with methylene chloride-water. The organic layer was washed with water, dried, and evaporated to dryness to give colorless syrups (0.77 g, 100%).

$^1$H-NMR (200 MHz, CDCl$_3$) δ: 0.95(3H, t), 1.05(3H, t), 1.60-1.87(4H, m), 2.88(2H, t), 3.92(2H, t), 5.26(2H, s), 5.58(1H, s), 7.40-7.80(8H, m).

REFERENCE EXAMPLE 10

1-(2'-Cyanobiphenyl-4-yl)methyl-6-phenylthio-3-propylpyrimidine-2,4(1H,3H)-dione A mixture of 6-chloro-1-(2'-cyanobiphenyl-4-yl)methyl-3-propylpyrimidine-2,4(1H,3H)-dione (1 g), thiophenol (0.33 ml) and potassium carbonate (0.44 g) in acetonitrile (20 ml) was heated under reflux for 5 hours. The reaction mixture was allowed to cool and the precipitate was removed by filtration. The filtrate was concentrated to dryness.

The resulting residue was purified by column chromatography on silica gel to give colorless syrups (1.1 g, 92%).

$^1$H-NMR (200 MHz, CDCl$_3$) δ: 0.93(3H, t), 1.58-1.76(2H, m), 3.88(2H, t), 5.06(2H, s), 5.35(1H, s), 7.41-7.70(12H, m), 7.78(1H, dd).

REFERENCE EXAMPLE 11

5,6-Dichloro-3-propyl-1-[[2'-(N-trityl-tetrazol-5-yl)biphenyl-4-yl]methyl]pyrimidine-2,4(1H,3H)-dione A mixture of 6-chloro-3-propyl-1-[[2'-(N-trityltetrazol-5-yl)biphenyl-4-yl]methyl]pyrimidine-2,4(1H,3H)-dione (0.6 g) and N-chlorosuccinimide (0.14 g) in chloroform (10 ml) was heated under reflux for 18 hours. The reaction mixture concentrated to dryness and the resulting residue was purified by column chromatography on silica gel to give colorless amorphous powders (0.22 g, 35%).

$^1$H-NMR (200 MHz, CDCl$_3$) δ: 0.96(3H, t), 1.00-1.79(2H, m), 3.96(2H, t), 5.21(2H, s), 6.86-6.94(6H, m), 7.11(4H, dd), 7.20-7.55(12H, m), 7.93-7.98(1H, m).

The following compounds (Reference Examples 12-28) were prepared according to the procedure for Reference Examples 2-5.

TABLE 3a

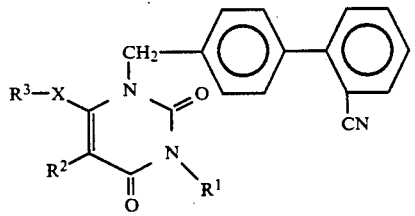

| Reference Example No. | R$^1$ | R$^2$ | —X—R$^3$ | MP. (°C.) |
|---|---|---|---|---|
| 12 | H | H | OPr | 203-204 |
| 13 | —CH$_2$COOEt | H | OPr | syrup |
| 14 | —CH$_2$COOEt | H | SPr | syrup |
| 15 | Pr | —CHO | SPr | syrup |
| 16 | —CH$_2$CON⌒N-Ph | H | Pr | powder |
| 17 | —CH$_2$CONHPh | H | Pr | powder |

TABLE 3a-continued

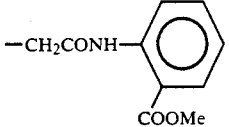

| Reference Example No. | R¹ | R² | —X—R³ | MP. (°C.) |
|---|---|---|---|---|
| 18 | —CH₂CONH—(C₆H₄)—COOMe | H | Pr | syrup |
| 19 | —CH₂CONHCH₂Ph | H | Pr | powder |
| 20 | —CH₂CONHCH₂—(2-pyridyl) | H | Pr | powder |

TABLE 3b

| Reference Example No. | $^1$H-NMR (200MHz, CDCl$_3$) α |
|---|---|
| 12 | (d⁶-DMSO): 0.82(3H, t), 1.58-1.75(2H,m), 4.01(2H, t), 5.04(2H, s), 5.12(1H, s), 7.39(2H, d), 7.54-7.63(4H, m), 7.74-7.82(1H, m), 7.94(1H, d), 11.17(1H, brs) |
| 13 | 0.96, 1.28(each 3H, t), 1.72-1.91(2H, m), 3.99(2H, t), 4.22 (2H, q), 4.71(2H, s), 5.16(3H, s), 7.39-7.69(7H, m), 7.76 (1H, d) |
| 14 | 1.05(3H, t), 1.28(3H, t), 1.70-1.88(2H, m), 2.89(2H, t), 4.22(2H, q), 4.72(2H, s), 5.28(2H, s), 5.62(1H, s), 7.39-7.78 (8H, m) |
| 15 | 0.93(3H, t), 0.98(3H, t), 1.51-1.70(2H, m), 1.64-1.83(2H, m), 2.97(2H, t), 3.99(2H, t), 5.62(2H, s), 7.44(4H, dd), 7.52-7.70(3H, m), 7.76(1H, d), 10.19(1H, s) |
| 16 | 1.00(3H, t), 1.55-1.72(2H, m), 2.45(2H, t), 3.16-3.30(4H, m), 3.67-3.84(4H, m), 4.88(2H, s), 5.21(2H, s), 5.75(1H, s), 6.88-6.97(3H, m), 7.24-7.34(4H, m), 7.41-7.69(5H, m), 7.76 (1H, d) |
| 17 | 1.01(3H, s), 1.52-1.70(2H, m), 2.46(2H, t), 4.82(2H, s), 5.21, (2H, s), 5.77(1H, s), 7.10(1H, brs), 7.31(4H, d), 7.41-7.69 (8H, m), 7.77(1H, d) |
| 18 | 1.02(3H, t), 1.58-1.74(2H, m), 2.49(2H, t), 3.88(3H, s), 4.89 (2H, s), 5.23(2H, s), 5.79(1H, s), 7.07(1H, t), 7.31-7.69 (8H, m), 7.77(1H, d), 8.01(1H, dd), 8.71(1H, dd) |
| 19 | 1.00(3H, t), 1.50-1.71(2H, m), 2.45(2H, t), 4.49(2H, d), 4.70 (2H, s), 5.21(2H, s), 5.74(1H, s), 5.99(1H, t), 7.25-7.36 (7H, m), 7.40-7.69(5H, m), 7.77(1H, d) |
| 20 | 0.99(3H, t), 1.52-1.71(2H, m), 2.44(2H, t), 4.59(2H, d), 4.77 (2H, s), 5.73(1H, s), 7.13-7.33(5H, m), 7.40-7.68(6H, m) |

TABLE 4a

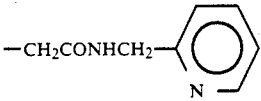

| Reference Example No. | R¹ | R² | —X—R³ | MP. (°C.) |
|---|---|---|---|---|
| 21 | —CH₂COOMe | H | Pr | powder |
| 22 | —CH₂COOEt | H | Pr | 189-191 |
| 23 | Et | H | Pr | powder |
| 24 | Bu | H | Pr | powder |

TABLE 4a-continued

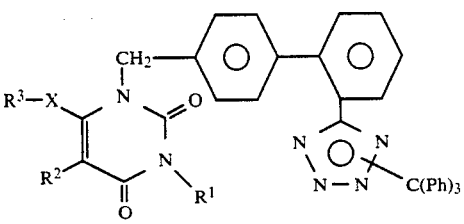

| Reference Example No. | R¹ | R² | —X—R³ | MP. (°C.) |
|---|---|---|---|---|
| 25 | Pr | Cl | Cl | powder |
| 26 | Pr | H | Cl | powder |
| 27 | Pr | H | Pr | powder |
| 28 | —CH₂(CH₂)₃COOMe | H | Pr | syrup |

TABLE 4b

| Reference Example No. | ¹H-NMR (200MHz, CDCl₃) α |
|---|---|
| 21 | 0.89(3H, t), 1.43-1.61(2H, m), 2.28(2H, t), 3.76(3H, s), 4.74(2H, s), 5.03(2H, s), 5.66(1H, s), 6.89-6.98(8H, m), 7.11(14H, m), 7.89-7.94(1H, m) |
| 22 | 0.88, 1.27(each 3H, t), 1.43-1.62(2H, m), 2.27(2H, t), 4.22 (2H, q), 4.73, 5.03(each 2H, s), 5.65(1H, s), 6.88-6.98 (8H, m), 7.13(2H, d), 7.20-7.53(12H, m), 7.88-7.93(1H, m) |
| 23 | 0.89, 1.26(each 3H, t), 1.42-1.61(2H, m), 2.27(2H, t), 4.05 (2H, q), 5.03(2H, s), 5.61(1H, s), 6.89-6.98(8H, m), 7.13 (2H, d), 7.21-7.54(12H, m), 7.89-7.94(1H, m) |
| 24 | 0.88, 0.95(each 3H, t), 1.33-1.73(6H, m), 2.26, 3.97 (each 2H, t), 5.02(2H, s), 5.60(1H, s), 6.89-6.98 (8H, m), 7.13(2H, d), 7.23-7.56(12H, m), 7.89-7.95(1H, m) |
| 25 | 0.96(3H, t), 1.60-1.79(2H, m), 3.96(2H, t), 5.21(2H, s), 6.86-6.94(6H, m), 7.11(4H, dd), 7.20-7.55(12H, m), 7.93-7.98(1H, m) |
| 26 | 0.94(3H, t), 1.58-1.75(2H, m), 3.89(2H, t), 5.14(2H, s), 5.88(1H, s), 6.87-6.93(6H, m), 7.07-7.51(16H, m), 7.91-7.97(1H, m) |
| 27 | 0.88, 0.96(each 3H, t), 1.42-1.61(2H, m), 1.60-1.78(2H, m), 2.26, 3.93(each 2H, t), 5.01(2H, s), 5.60(1H, s), 6.89-6.96 (8H, m), 7.09-7.52(14H, m), 7.88-7.93(1H, m) |
| 28 | 0.88(3H, t), 1.43-1.61(2H, m), 1.66-1.77(4H, m), 2.27(2H, t), 2.33-2.42(2H, m), 3.64(3H, s), 3.96-4.04(2H, m), 5.02(2H, s), 5.60(1H, s), 6.89-6.98(8H, m), 7.10-7.53(14H, m), 7.89-7.95 (1H, m) |

REFERENCE EXAMPLES 29-38

The following starting compounds were prepared according to the methods described in references (1)-(15) as mentioned above.

TABLE 5

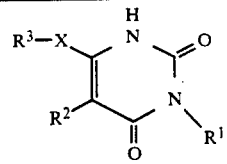

| Reference Example No. | R¹ | R² | —X—R³ | MP. (°C.) |
|---|---|---|---|---|
| 29 | Pr | H | Cl | 196-200 |
| 30 | Et | H | Cl | 215-217 |
| 31 | Bu | H | Cl | 193-196 |
| 32 | Pr | Ph | Cl | 230-231 |
| 33 | Et | H | Pr | 168-169 |
| 34 | Pr | H | Pr | 169-170 |
| 35 | Bu | H | Pr | 161-164 |
| 36 | —CH₂COOMe | H | Pr | 163-165 |
| 37 | —CH₂COOEt | H | Pr | 167-170 |

TABLE 5-continued

| Reference Example No. | R¹ | R² | —X—R³ | MP. (°C.) |
|---|---|---|---|---|
| 38 | —CH₂(CH₂)₃COOMe | H | Pr | 98-99 |

EXPERIMENTAL EXAMPLE 1

Inhibition of Binding of Angiotensin-II to Angiotensin Receptor

Method

An experiment of inhibition on the binding of angiotensin-II (A-II) to A-II-receptor was conducted by modifying the method of Douglas et al. [Endocrinology, 102, 685-696 (1978)]. An A-II-receptor was prepared from the membrane fraction of bovine adrenal cortex.

The compound of the present invention ($10^{-6}$M to $10^{-8}$M) and $^{125}$I-A-II (1.85 kBq/50 μl) were added to the receptor membrane fraction, and the mixture was incubated at room temperature for one hour. The receptor-bound and free $^{125}$I-A-II were separated through a filter (Whatman GF/B filter), and the radioactivity of $^{125}$I-A-II bound to the receptor was measured.

Results

The results relating to the compounds of the present invention are shown in Table 6.

EXPERIMENTAL EXAMPLE 2

Inhibitory Effect of the Compound of the Present Invention on Pressor Action of A-II

Method

Jcl: SD rats (9 week old, male) were used. On the day previous to the experiment, these animals were applied with cannulation into the femoral artery and vein under anesthesia with pentobarbital Na. The animals were fasted but allowed to access freely to drinking water until the experiment was started. Just on the day of conducting the experiment, the artery cannula was connected with a blood-pressure transducer, and the average blood pressure was recorded by means of polygraph. Before administration of the drug, the pressor action due to intravenous administration of A-II (100 ng/kg) as the control was measured. The drugs were orally administered, and then, at each point of the measurement, A-II was administered intravenously, and the pressor action was similarly measured. By comparing the pressor action before and after administration of the drug, the percent inhibition by the drug on A-II-induced pressor action was evaluated.

Results

The results relating to the compounds of the present invention are shown in Table 6.

TABLE 6

| Working Example No. | Angiotensin II Receptor Binding $IC_{50}$ ($\mu$M) | Pressor Response to A II (30 mg/Kg, p.o.) |
|---|---|---|
| 1 | 0.86 | NT*[1] |
| 2 | 0.02 | +++*[2] |
| 3 | 0.02 | NT |
| 4 | 0.04 | +++ |
| 5 | 0.32 | + |
| 6 | 0.02 | + |
| 7 | 0.33 | − |
| 8 | 0.06 | +++ |
| 9 | 0.04 | +++ |
| 10 | 0.32 | − |
| 14 | 0.34 | − |
| 16 | 2.66 | NT |
| 18 | 0.14 | +++ |
| 23 | 0.02 | +++ |
| 25 | 0.02 | +++ |
| 26 | 0.02 | +++ |
| 27 | 0.01 | +++ |
| 28 | 0.02 | +++ |

*[1]NT, not tested.
*[2]% Inhibition. +++ ≧ 70 > ++ ≧ 50 > + ≧ 30 > −.

It is understood that the preceding representative examples may be varied within the scope of the present invention by one skilled in the art to achieve essentially the same results.

As many widely different embodiments of this invention may be made without departing from the spirit and scope thereof, it is to be understood that this invention is not limited to the specific embodiments thereof except as defined in the appended claims.

The following references, which are referred to for their disclosures at various points in this application, are incorporated herein by reference.

1. M. A. Ondetti and D. W. Cushman, Annual Reports in Medicinal Chemistry, 13, 82–91 (1978).
2. Japanese Patent Laid Open No. 71073/1981.
3. Japanese Patent Laid Open No. 71074/1981.
4. Japanese Patent Laid Open No. 92270/1982.
5. Japanese Patent Laid Open No. 157768/1983.
6. Japanese Patent Laid Open No. 23868/1988.
7. Japanese Patent Laid Open No. 117876/1989.
8. A. T. Chiu et al., Eur. J. Pharm., 157, 13 (1981).
9. P. C. Wong et al., J. Pharmcol. Exp. Ther., 247, 1 (1988).
10. P. C. Wong et al., Hypertension, 13, 489 (1989).
11. Chem. Ber., 95, 1597, (1962).
12. Ann. Chem., 691, 142, (1966).
13. G. W. Anderson, I. F. Halverstadt, W. H. Miller and R. O. Roblin, J. Am. Chem. Soc., 67, 2197 (1945).
14. E. Coats, W. R. Glave and C. Hansch, J. Med. Chem., 13, 913 (1970).
15. F. H. S. Curd, D. N. Richardson and F. L. Rose, J. Chem. Soc., 343 (1946).
16. T. Kinoshita, N. Nakahata, A. Kouchi and S. Furukawa, Chem. Pharm. Bull., 36, 3887 (1988).
17. J. P. Horwitz and A. J. Tomson, J. Org. Chem., 26, 3392 (1961).
18. R. Kaul and B. Hempel, Arzneim.-Forsch., 32, 722 (1982).
19. J. A. Hendry and R. F. Homer, J. Chem. Soc., 328 (1952).
20. S. B. Greenbaum and W. L. Holmes, J. Am. Chem. Soc., 76, 2899 (1954).
21. K. Tanaka, T. Kimura, T. Okada, X. Chen and F. Yoneda, Chem. Pharm. Bull., 35, 1397 (1987).
22. K. Edo, T. Sakamoto and H. Yamanaka, Chem. Pharm. Bull., 26, 3843 (1978).
23. R. Kaul, G. Kiefer and B. Hempel, Arzeim.-Forsch., 32, 610 (1982).
24. G. Kiefer, R. Kaul, K. Keppeler and B. Hempel, Arch. Pharm., 315, 444 (1982).
26. Y. Ikoma, S. Higuchi and Y. Naoi, Japanese Patent Laid Open No. 83072/1989.
27. J. R. E. Hoover, A. W. Chow, R. J. Stedman, N. M. Hall, H. S. Greenberg, M. M. Dolan and R. J. Feriauto, J. Med. Chem., 7, 245 (1964).
28. R. J. Stedman, J. R. E. Hoover, A. W. Chow, M. M. Dolan, N. M. Hall and R. J. Feriauto, J. Med. Chem., 7, 251 (1964).
29. H. Gilman and R. D. Gorsich, J. Am. Chem. Soc., 78, 2217 (1956).
30. M. Orchin and E. Oscar Woolfolk, J. Am. Chem. Soc., 67, 122 (1945).
31. Douglas et al., Endocrinology, 102, 685–696 (1978).

What is claimed is:

1. A compound of the formula:

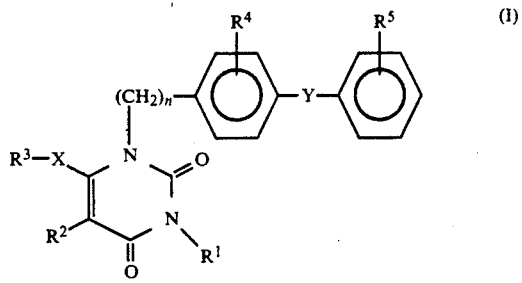

wherein $R^1$ is (i) hydrogen; (ii) a $(C_{1-8})$alkyl or $(C_{2-8})$alkenyl either of which can be substituted with carboxyl, $(C_{1-4})$alkoxycarbonyl or substituted carbamoyl; (iii) phenyl or naphthyl which can be substituted with halogen, nitro or $(C_{1-4})$alkyl; or (iv) phenyl-$(C_{1-4})$alkyl which can be substituted with halogen, nitro or ($C_{1-4}$)alkyl;

$R^2$ is hydrogen; halogen; nitro; formyl; amino; NH($C_{1-8}$)alkanoyl;

a group of the formula $NR^7R^8$ wherein $R^7$ and $R^8$ are independently hydrogen, ($C_{1-8}$)alkyl or ($C_{1-8}$)alkanoyl;

($C_{1-8}$)alkyl or ($C_{2-8}$)-alkenyl where the alkyl or alkenyl group can be substituted by nitrile, carbamoyl, phenyl, hydroxyl, carboxyl, ($C_{2-5}$)alkanoyloxy, ($C_{1-4}$)alkoxycarbonyl, amino, ($C_{1-4}$)alkylamino, di($C_{1-4}$)alkylamino, or ($C_{2-5}$)alkanoylamino;

groups of the formula:

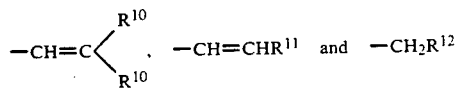

wherein $R^{10}$ is nitrile, carbamoyl, or lower alkoxycarbonyl, $R^{11}$ is ($C_{1-8}$)alkyl, phenyl, cyano, carbamoyl or lower alkoxycarbamoyl and $R^{12}$ is ($C_{1-2}$)dialkylamino, morpholino, piperidino or piperazino;

phenyl or naphthyl which can be substituted with 1-3 substituents from the group consisting of halogen, nitro, and ($C_{1-4}$)alkyl; or phenyl-($C_{1-4}$)alkyl which can be substituted with 1-3 three substituents selected from halogen, nitro, and ($C_{1-4}$)alkyl;

$R^3$ is ($C_{1-8}$)alkyl or ($C_{2-8}$)alkenyl either of which can be substituted with nitrile, carbamoyl, phenyl, hydroxyl, carboxyl, ($C_{2-5}$)alkanoyloxy, ($C_{1-8}$)alkoxycarbonyl, amino, ($C_{1-4}$)alkylamino or ($C_{2-5}$)alkanoylamino;

phenyl which can be substituted with 1-3 substituents selected from halogen, ($C_{1-4}$)alkyl and nitro; or phenyl-($C_{1-4}$)alkyl which can be further substituted with 1-3 substituents selected from halogen, nitro, and ($C_{1-4}$)alkyl;

$R^4$ is hydrogen, halogen or nitro;

$R^5$ is a group capable of forming an anion or convertible into an anion of the class consisting of carboxyl, ($C_{1-4}$)alkoxycarbonyl, cyano, tetrazolyl, $NHSO_2CF_3$, phosphoric acid, sulfonic acid which group can be protected with a ($C_{1-4}$)alkyl, ($C_{2-6}$)alkanoyloxy-($C_{1-4}$) alkyl, ($C_{1-6}$)alkoxy-($C_{1-4}$)alkyl or ($C_{1-6}$)alkoxycarbonyloxy-($C_{1-4}$) alkyl;

X is a bond or a spacer of the class consisting of —O—, —S—,

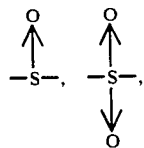

and an imino group having the formula:

wherein $R^9$ is hydrogen, ($C_{1-4}$)alkanoyl or ($C_{1-4}$)alkyl;

Y is a bond or a spacer selected from the class consisting of ($C_{1-4}$)alkylene, —C(=O)—, —O—, —S—, —NH—, —C(=O)—NH—, —O—$CH_2$, —S—$CH_2$—, and —CH=CH—;

n is 1 or 2 or a pharmaceutically acceptable salt thereof.

2. A compound according to claim 1, wherein $R^1$ is a ($C_{1-8}$)alkyl or ($C_{2-8}$)alkenyl either of which can be substituted with carboxyl, ($C_{1-4}$)alkoxycarbonyl or substituted carbamoyl.

3. A compound according to claim 1, wherein $R^2$ is a alkyl of 1 to 8 carbon atoms or alkenyl of 2 to 8 carbon atoms, either of which may be substituted with nitrile, carbamoyl, phenyl, hydroxyl, carboxyl, $C_{2-5}$ alkanoyloxy, $C_{1-4}$ alkoxycarbonyl, amino, lower ($C_{1-4}$) alkylamino, di-lower ($C_{1-4}$) alkylamino, or ($C_{2-5}$) alkanoylamino.

4. A compound according to claim 1, wherein $R^2$ is selected from the class consisting of

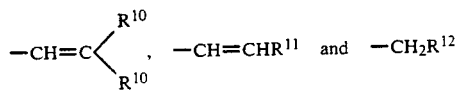

wherein
$R^{10}$ is nitrile, carbamoyl, or alkoxycarbonyl and
$R^{11}$ is ($C_{1-8}$) alkyl, phenyl, cyano, carbamoyl, or $C_{1-8}$ alkoxycarbonyl and
$R^{12}$ is dimethylamino, diethylamino, morpholino, piperidino, or piperazino.

5. A compound according to claim 1, wherein $R^3$ is alkyl of 1 to 8 carbon atoms or alkenyl of 2 to 8 carbon atoms, which may be straight or branched and may be substituted with nitrile, carbamoyl, phenyl, hydroxyl, carboxyl, $C_{2-5}$ alkanoyloxy, $C_{1-4}$ alkoxycarbonyl, amino, ($C_{1-4}$) alkylamino or ($C_{2-5}$) alkanoylamino.

6. A compound according to claim 1, wherein $R^1$ optionally is phenyl which may be optionally substituted with 1 to 3 substituents selected from the class consisting of halogen, nitro and lower ($C_{1-4}$) alkyl.

7. A compound according to claim 1, wherein $R^1$ is phenyl-lower ($C_{1-4}$) alkyl which may be substituted with 1 to 3 substituents selected from the class consisting of halogen, nitro and lower ($C_{1-4}$) alkyl.

8. A compound according to claim 7, wherein the phenyl-lower ($C_{1-4}$) alkyl is benzyl or phenethyl.

9. A compound according to claim 1, wherein $R^2$ is a group having the formula: —$HNR^6$ or a group having the formula:

wherein $R^6$ is an alkanoyl group of 1 to 8 carbon atoms derived from fatty acid, and $R^7$ and $R^8$ each is independently hydrogen, lower alkyl of 1 to about 8 carbon atoms or an alkanoyl group of 1 to 8 carbon atoms derived from fatty acid.

10. A compound according to claim 1, wherein $R^2$ is phenyl which may be substituted with 1 to 3 substituents selected from the class consisting of halogen, nitro and lower ($C_{1-4}$) alkyl.

11. A compound according to claim 1, wherein $R^2$ is phenyl-lower ($C_{1-4}$) alkyl which may be substituted with 1 to 3 substituents selected from the class consisting of halogen, nitro and lower ($C_{1-4}$) alkyl.

12. A compound according to claim 11, wherein the phenyl-lower ($C_{1-4}$) alkyl is benzyl or phenethyl.

13. A compound according to claim 1, wherein $R^3$ is phenyl which may be substituted with 1 to 3 substituents selected from the class consisting of halogen, nitro and lower ($C_{1-4}$) alkyl.

14. A compound according to claim 1, wherein $R^3$ is phenyl-lower ($C_{1-4}$) alkyl which may be substituted with 1 to 3 substituents selected from the class consisting of halogen, nitro and lower ($C_{1-4}$) alkyl.

15. A compound according to claim 14, wherein the phenyl-lower ($C_{1-4}$) alkyl is benzyl or phenethyl.

16. A compound according to claim 1, wherein $R^5$ is carboxyl, lower ($C_{1-4}$) alkoxycarbonyl, cyano, tetrazolyl, trifluoromethanesulfonic amide ($-NHSO_2CF_3$), phosphoric acid, or sulfonic acid.

17. A compound according to claim 1, wherein $R^5$ is in the ortho position.

18. A compound according to claim 1, wherein $R^5$ is tetrazolyl.

19. A compound according to claim 1, wherein the group Y is a direct bond.

20. A compound according to claim 1, which is a compound of the formula (I'):

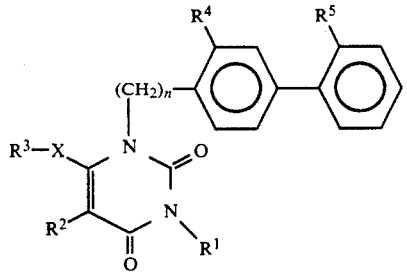

wherein $R^1$ is lower ($C_{2-5}$) alkyl, which may be substituted with carboxyl, lower ($C_{1-4}$) alkoxycarbonyl or substituted carbamoyl; $R^2$ is hydrogen; $R^3$ is lower ($C_{2-5}$) alkyl, which may be substituted with ($C_{1-4}$) alkoxycarbonyl; X is a direct bond, $-S-$, $-S(O)-$, $-S(O)_2-$, $-O-$, $-NH-$ or $-N(\text{lower } C_{2-5})\text{alkyl})-$; $R^4$ is hydrogen, halogen or nitro; and $R^5$ is carboxyl or tetrazolyl; or a pharmaceutically acceptable salt thereof.

21. A compound according to claim 1 or a pharmaceutically acceptable salt thereof, which is selected from the group consisting of 6-ethylthio-3-propyl-1-[[2'-(1H-tetrazol-5-yl)biphenyl-4-yl]methyl]-pyrimidine-2,4(1H,3H)-dione, 3-ethyl-6-propyl-1-[[2'-(1H-tetrazol-5-yl)biphenyl-4-yl]methyl]pyrimidine-2,4(1H,3H)-dione, 3-propyl-6-propyl-1-[[2'-(1H-tetrazol-5-yl)biphenyl-4-yl]methyl]pyrimidine-2,4(1H,3H)-dione, 3-butyl-6-propyl-1-[[2'-(1H-tetrazol-5-yl)biphenyl-4-yl]methyl]-pyrimidine-2,4(1H,3H)-dione, 3-methoxycarbonylmethyl-6-propyl-1-[[2'-(1H-tetrazol-5-yl)biphenyl-4-yl]methyl]pyrimidine-2,4(1H,3H)-dione, 3-ethoxycarbonylmethyl-6-propyl-1-[[2'-(1H-tetrazol-5-yl)biphenyl-4-yl]methyl]pyrimidine-2,4(1H,3H)-dione, and 3-ethoxycarbonylmethyl-3-propyl-1-[[2'-(1H-tetrazol-5-yl)biphenyl-4-yl]methyl]pyrimidine-2,4(1H,3H)-dione.

22. A pharmaceutical composition for antagonizing angiotensin II which comprises a therapeutically effective amount of a compound according to claim 1 or a pharmaceutically acceptable salt thereof in admixture with a pharmaceutical acceptable carrier, excipient or diluent.

23. A method for antagonizing angiotensin II in a mammal which comprises administering a thereapeutically effective amount of a compound according to claim 1 or a pharmaceutically acceptable salt thereof.

* * * * *